US012098005B2

(12) United States Patent
Martella et al.

(10) Patent No.: US 12,098,005 B2
(45) Date of Patent: Sep. 24, 2024

(54) WATER BOTTLE CAP ASSEMBLIES

(71) Applicant: UNITED STATES ENDOSCOPY GROUP, INC., Mentor, OH (US)

(72) Inventors: Tony Martella, Mentor, OH (US); Michael Simenc, Sagamore Hills, OH (US); Gary E. Mann, Painesville, OH (US); Roger Popelka, Chesterland, OH (US); Megan Hieber, Auburn Township, OH (US); Joseph Mrva, Kirtland, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 211 days.

(21) Appl. No.: 17/332,293

(22) Filed: May 27, 2021

(65) Prior Publication Data
US 2021/0371175 A1 Dec. 2, 2021

Related U.S. Application Data

(60) Provisional application No. 63/030,520, filed on May 27, 2020.

(51) Int. Cl.
*B65D 51/24* (2006.01)
*A61B 1/00* (2006.01)
(Continued)

(52) U.S. Cl.
CPC .......... *B65D 51/24* (2013.01); *A61B 1/00131* (2013.01); *A61B 1/015* (2013.01); *B65D 45/325* (2013.01)

(58) Field of Classification Search
CPC ...... B65D 51/24; B65D 43/325; A61B 1/015; A61B 1/0013; A61B 1/0012; A61B 1/00119
(Continued)

(56) References Cited

U.S. PATENT DOCUMENTS

D114,053 S    4/1939  Barnes
D123,648 S   11/1940  Holdren
(Continued)

FOREIGN PATENT DOCUMENTS

EP     2627235 B1    8/2013
WO  2017173426 A1   10/2017

OTHER PUBLICATIONS

Endo SmartCap Brochure: http://www.medivators.com/sites/default/files/pdf/50098-246D_ENDOGATOR_SMARTCAP.pdf.
(Continued)

*Primary Examiner* — Ernesto A Grano
*Assistant Examiner* — Symren K Sanghera
(74) *Attorney, Agent, or Firm* — Calfee, Halter & Griswold LLP

(57) ABSTRACT

Embodiments of the present invention provide water bottle cap assemblies suitable for attachment to an endoscopic device and a water source. The water bottle cap assembly can include a plurality of ports and an engageable member to sealingly engage the cap with a water source. The assembly also includes a plurality of tubular members, each tubular member coupled to a respective port so as to be in fluid communication therewith. The assembly can include a cap having a grippable surface that is overmolded onto the cap. The cap can also have a soft inner seal on the interior surface, and the soft inner seal can be integrally formed with the overmolded grippable surface. The cap can have a top that is pressfit onto the main portion of the cap. The grippable surface material can be overmolded over the top of the cap.

10 Claims, 23 Drawing Sheets

(51) Int. Cl.
  *A61B 1/015* (2006.01)
  *B65D 45/32* (2006.01)
(58) Field of Classification Search
  USPC .......................................................... 215/228
  See application file for complete search history.

(56) References Cited

U.S. PATENT DOCUMENTS

| | | | |
|---|---|---|---|
| D137,702 S | 4/1944 | Conman | |
| D156,280 S | 11/1949 | Rosenthal | |
| D225,308 S | 12/1972 | Barefoot | |
| D327,016 S | 6/1992 | Leuenberger | |
| D349,647 S | 8/1994 | Moffitt | |
| 5,875,915 A * | 3/1999 | Bradshaw | B65D 43/0218 |
| | | | 206/508 |
| D433,275 S | 11/2000 | Betras | |
| 6,210,322 B1 | 4/2001 | Byrne | |
| 6,485,412 B1 | 11/2002 | Byrne | |
| D494,468 S | 8/2004 | Vovan | |
| D528,925 S | 9/2006 | Barone | |
| D580,758 S | 11/2008 | Lacov | |
| D590,255 S | 4/2009 | Maxwell | |
| 7,552,831 B2 * | 6/2009 | Catton | A61J 11/04 |
| | | | 215/11.1 |
| D616,822 S | 6/2010 | Zayas | |
| D630,044 S | 1/2011 | Lane | |
| D642,918 S | 8/2011 | Taylor | |
| D656,819 S | 4/2012 | Porter | |
| D673,814 S | 1/2013 | Honein | |
| D675,096 S | 1/2013 | Obrist | |
| D681,464 S | 5/2013 | Taylor | |
| D706,631 S | 6/2014 | Wilson | |
| 9,144,373 B2 | 9/2015 | Kaye et al. | |
| D744,857 S | 12/2015 | Gieske | |
| D748,776 S | 2/2016 | Brannon | |
| D757,546 S | 5/2016 | Seifer | |
| 9,731,875 B2 | 8/2017 | Wilson | |
| D832,795 S | 11/2018 | Maegawa | |
| D837,976 S | 1/2019 | Kaye | |
| 10,456,014 B2 | 10/2019 | Wolcott et al. | |
| D872,521 S | 1/2020 | Sitwell | |
| 10,653,255 B1 * | 5/2020 | Trawinski | B65D 50/064 |
| D895,421 S | 9/2020 | Laible | |
| D899,925 S | 10/2020 | Laible | |
| D902,430 S | 11/2020 | Jones | |
| D932,048 S | 9/2021 | Laible | |
| D936,731 S | 11/2021 | Jin | |
| D954,497 S | 6/2022 | Roberts | |
| D957,184 S | 7/2022 | Mccready | |
| D957,877 S | 7/2022 | Waggoner | |
| 2008/0142471 A1 * | 6/2008 | Yorita | B65D 51/2842 |
| | | | 215/228 |
| 2008/0308519 A1 * | 12/2008 | Farrar | B65D 51/145 |
| | | | 215/44 |
| 2008/0308554 A1 | 12/2008 | Farrar et al. | |
| 2010/0133227 A1 | 6/2010 | Ver Hage | |
| 2011/0263939 A1 | 10/2011 | Kaye et al. | |
| 2012/0103849 A1 * | 5/2012 | Rachuk | G09F 9/00 |
| | | | 206/459.1 |
| 2014/0088432 A1 * | 3/2014 | Ryan | A61B 10/0283 |
| | | | 600/562 |
| 2014/0265313 A1 * | 9/2014 | Durr | A61B 1/0014 |
| | | | 285/305 |
| 2015/0297063 A1 * | 10/2015 | Wolcott | A61B 1/00128 |
| | | | 600/158 |
| 2016/0325582 A1 * | 11/2016 | Werner | B60B 3/10 |
| 2017/0280976 A1 * | 10/2017 | Roberts | A61B 1/12 |
| 2019/0039790 A1 * | 2/2019 | Therrien | B65D 47/06 |
| 2019/0090725 A1 | 3/2019 | Roberts | |
| 2019/0106251 A1 * | 4/2019 | Sterling | B65D 41/3447 |
| 2019/0110665 A1 | 4/2019 | Mann | |
| 2019/0117046 A1 | 4/2019 | Briggs | |
| 2019/0256260 A1 * | 8/2019 | Carver | B65D 45/325 |

OTHER PUBLICATIONS

Erbeflo CleverCap Brochure: https://us.erbe-med.com/fileadmin/user_upload/ERBEFLO-CleverCap-_MKT5058-03-2017-01_.pdf.
International Search Report from PCT/US2021/034502 dated Dec. 14, 2021.
Restriction Requirement from U.S. Appl. No. 29/736,045 dated Jun. 17, 2022.
Office Action from U.S. Appl. No. 29/736,045 dated Aug. 31, 2022.
Steris. AquaShield® Water Bottle System. https://www.steris.com/healthcare/products/endoscopy-devices/gi-bleed-management-and-irrigation/aguashield-water-bottle-system (downloaded Apr. 21, 2022).
AquaShield® water bottle system. Mar. 2015. https://www.boucartmedical.com/wp-content/uploads/2015/03/aguashield.pdf (Year: 2015).
Steris Endoscopy. Irrigation Accessories. Mar. 2022. https://diagmed.healthcare/wp-content/uploads/2022/03/Irrigation-Accessories.pdf (Year: 2022).

* cited by examiner

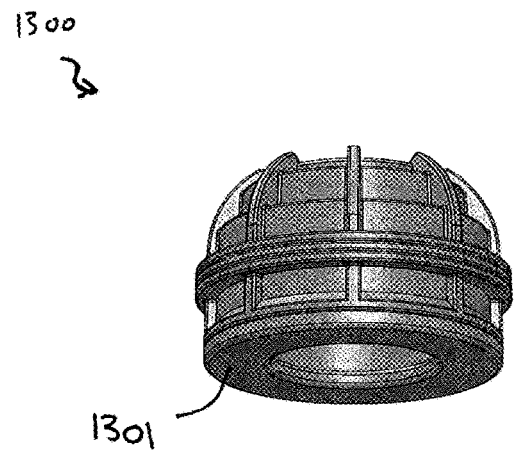
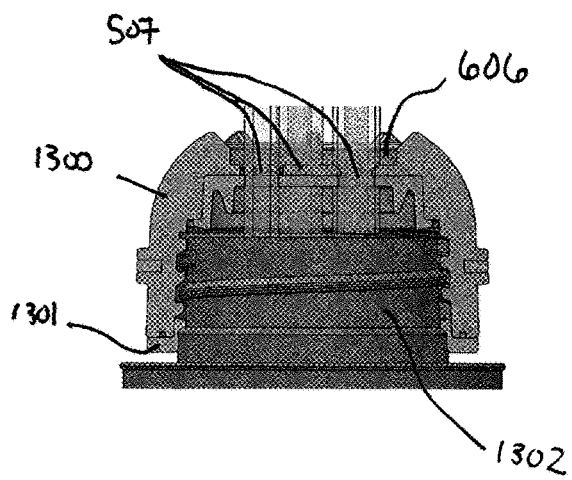
FIG. 13A  FIG. 13B
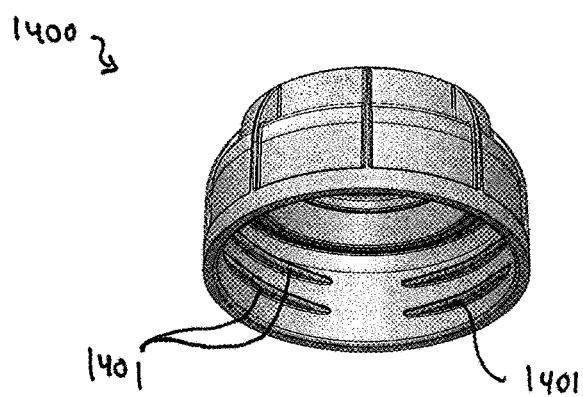
FIG. 14

WATER BOTTLE CAP ASSEMBLIES

CROSS-REFERENCE TO RELATED APPLICATIONS

The present application claims benefit and priority to U.S. Provisional Patent Application No. 63/030,520, filed on May 27, 2020, the entire disclosure of which is incorporated herein by reference.

FIELD OF THE INVENTION

The present application is directed to devices used in surgical procedures, such as endoscopic procedures, and more particularly to a water bottle cap assemblies that can be connected to a water bottle and an apparatus, such as an endoscopic device.

BACKGROUND

Many invasive medical procedures that previously required major surgery are now performed using endoscopic instruments. Such instruments can provide an internal view of particular body parts, organs, or passages without requiring invasive surgery. Generally, an endoscopic instrument may include one or more channels through which miniaturized, flexible instruments can be inserted and advanced. The endoscope typically includes an elongated flexible insertion tube equipped at one end with an eyepiece or other viewing means and at the other end with an optical lens. The insertion tube transmits images or image-producing signals from the illuminated operative site to the viewing means to provide the instrument operator with full vision of the actions being performed at the instrument's working end.

The insertion tube of an endoscope also provides a flow passage for the delivery of fluid (e.g., liquid or gas) for irrigation, insufflation or other purposes. In conventional practice, it is necessary to provide a flow of sterile water across the optic lens to prevent the buildup of materials (e.g., surgical debris and body fluids) on the optic lens. This flow of water operates, in a sense, like a windshield wiper/washer assembly.

In common designs, an endoscopic instrument typically has a control body which is connected by a light guide tube to a light guide connector, which includes a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic lens of the instrument.

For example, FIG. 1 illustrates an endoscope system 100. The endoscope is shown to include a shaft (insertion tube) connected to a control body that includes a biopsy port, air-water and suction valves, and angulation controls. The control body is connected to an umbilical (light guide connecting tube) that further connects to an electrical pin unit, which is directly connected to a light source and is connected via a video connection lead (and plug) to a video processor. Each of the tubes extends from the control body to a main body for effecting various connections to the endoscopic device (e.g., air/water bottle connection suction, etc.). The image produced by the endoscope is transmitted via a fiber optic bundle, or electronically from a charge-coupled device (CCD) chip. FIG. 1 illustrates a video monitor and attached keyboard for viewing images and inputting commands. The main body includes a port for a water bottle connector that connects to a water bottle for providing water to the endoscope.

The somewhat complex internal anatomy of the endoscope is further illustrated in FIG. 2, which shows a detailed view of the endoscope from FIG. 1. As shown in FIG. 2, the shaft incorporates an instrumentation channel extending from the entry biopsy port to the tip of the instrument.

Unexpectedly, there is usually a great expense associated with the delivery of sterile water in an endoscopy system. As shown in FIG. 1, the known practice has been to use a water bottle with a cap having a tube. This tube typically has a fitting at the end distal to the bottle to allow for connection to the air/water bottle connector port seen in FIG. 2. This fitting is usually specific to the particular endoscope manufacturer, such as Olympus®, Fujinon®, or Pentax®.

Ambient air is often pumped into the system to charge the water bottle. It can be desirable, however, to provide a secondary gas source to the endoscope instead of ambient air, such as carbon dioxide ($CO_2$). Irrigation may also be desired during an endoscopic procedure. However, a separate connection, pump, and water source are conventionally required in order to effectuate irrigation through the endoscopic device.

Therefore, there is a need for a water bottle cap assembly that is easily manufactured and cost effective. There is a need for a water bottle cap assembly that is configured to seal with a variety of bottles and endoscopes. There is also a need for a water bottle cap assembly that is configured for use with a variety of endoscopic instruments, procedures (e.g., lens cleaning, secondary gas, and/or irrigation), and water sources. There is also a need for a water bottle cap assembly that is assembled without requiring an adhesive.

SUMMARY OF THE INVENTION

Embodiments of the present invention provide water bottle cap assemblies for use in endoscopy procedures. The inventive water bottle cap assemblies can be designed and shaped to function with endoscopic devices generally or may be designed and shaped to function with endoscopic devices having a particular structure unique to a single manufacturer of endoscopic devices. Similarly, the water bottle cap assemblies may be configured for use with a variety of different water sources. In light of their economical nature (and option for disposable, single or daily use), the exemplary embodiments of water bottle cap assemblies described herein allow for provision of a secondary gas in an endoscopy. In one embodiment, the water bottle cap is configured to also support irrigation. These and other benefits are more fully described herein.

In certain embodiments, the present invention provides water bottle cap assemblies that can be used with endoscopic devices. In particular, the water bottle cap assemblies allow for in-line placement between the endoscopic device and a water source. For example, the water bottle cap assembly may include a cap comprising a plurality of ports (e.g., two, three, four, etc.) and an engageable member (e.g., internal threads) configured to sealingly engage with a water source (e.g., a water bottle or suitable container for holding one or more fluids). The assembly also includes a plurality of tubular members, each tubular member coupled to a respective port so as to be in fluid communication therewith. The tubular members may be single or dual lumen for conveying fluid between the water source and the endoscopic device. The ports to which the tubular members attach may extend from a piece that is pressfit into place as the top of the water bottle cap. The ports to which the tubular members attach may also be overmolded onto the cap. The ports may also be pressfit to the top of the cap. In addition, the assembly includes an adaptor coupled to an end of one of the tubular members that is configured to engage with an endoscopic device. At least one of the tubular members may be configured to convey at least one fluid (e.g., water, air, or secondary gas) between the water source and the endoscopic device.

BRIEF DESCRIPTION OF THE DRAWINGS

Figure 1:
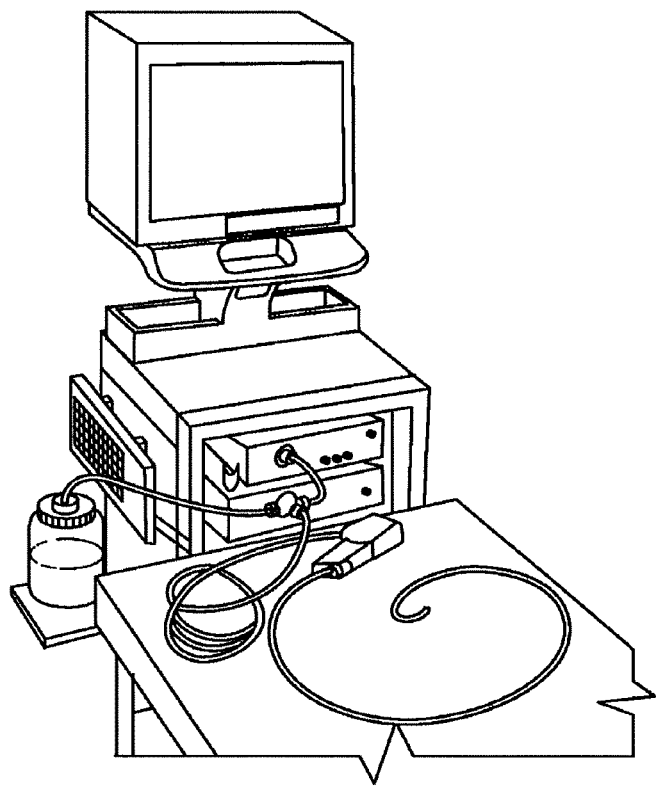
Figure 2:
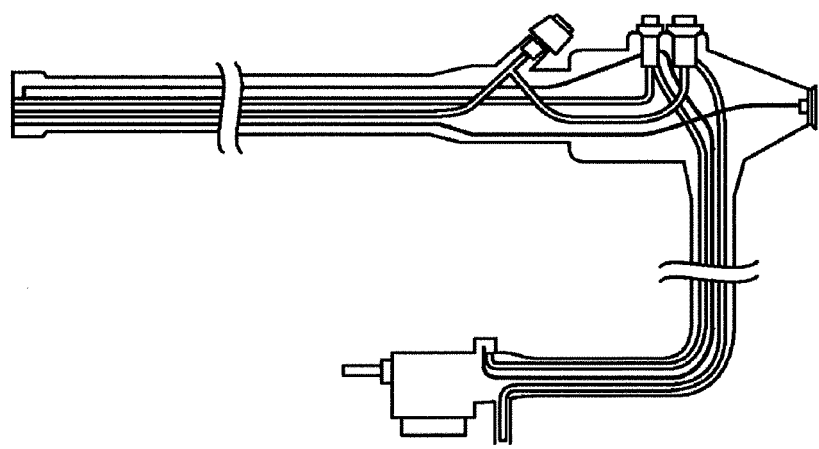
Figure 3:
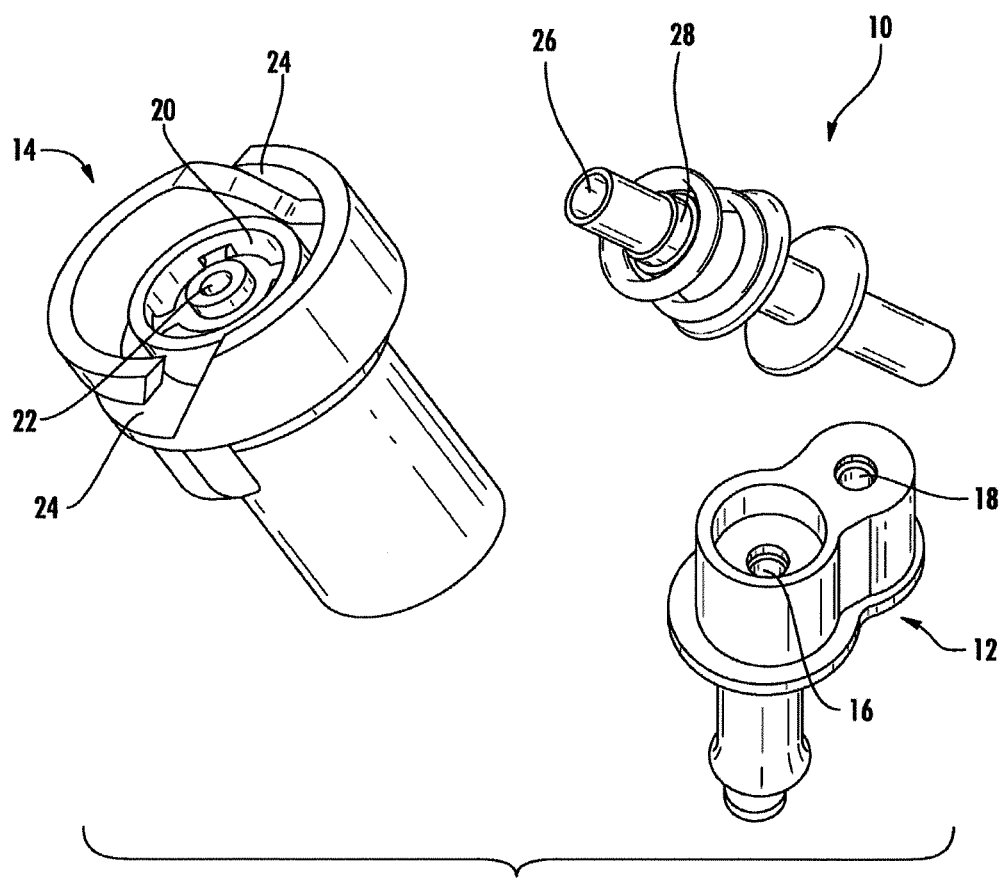
Figure 4:
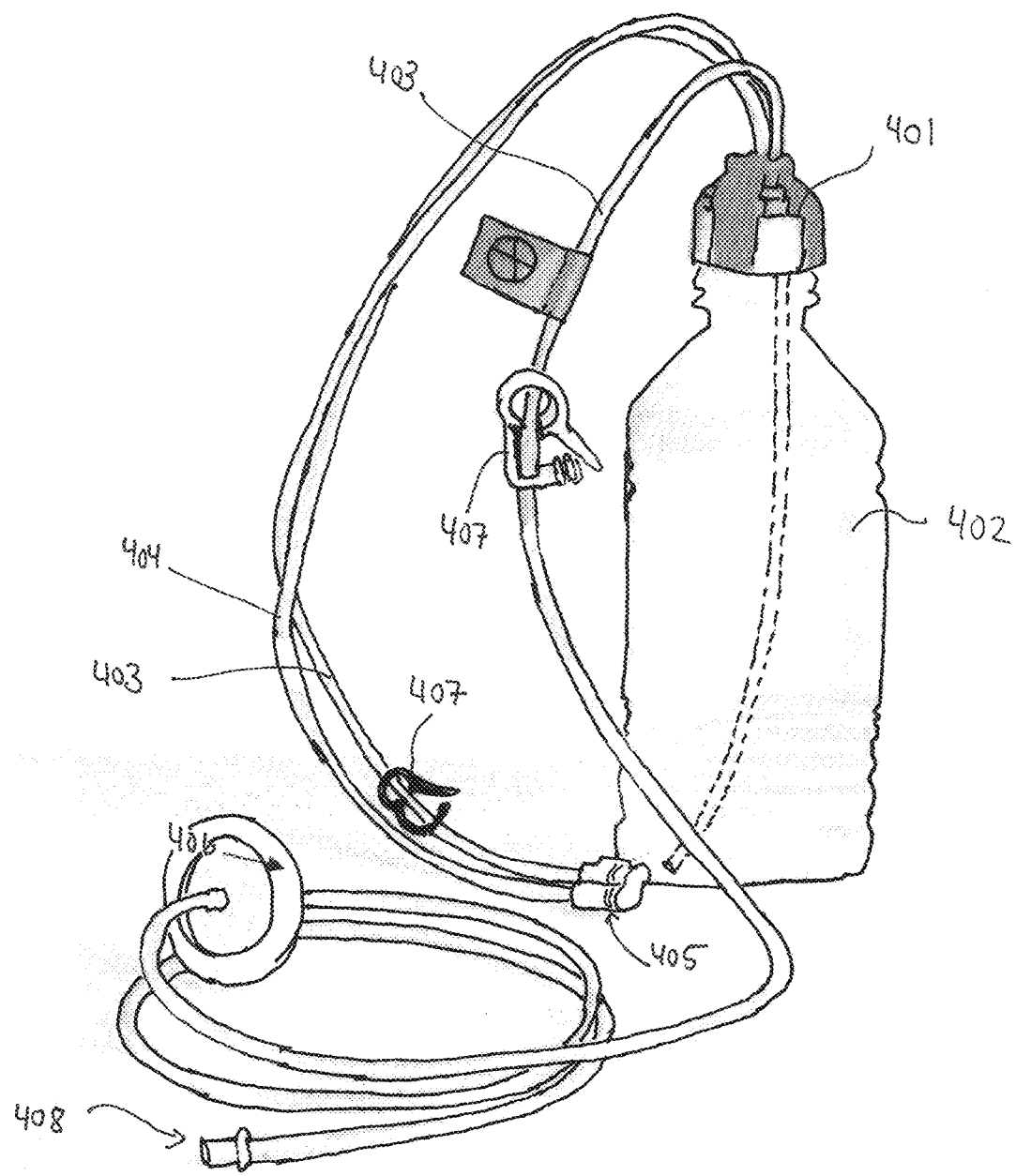
Figure 5A:
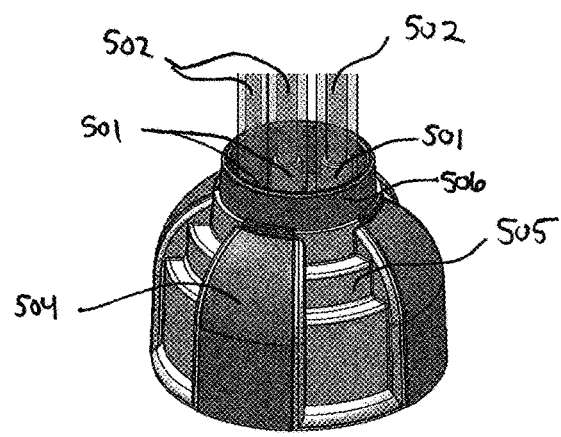
Figure 5B:
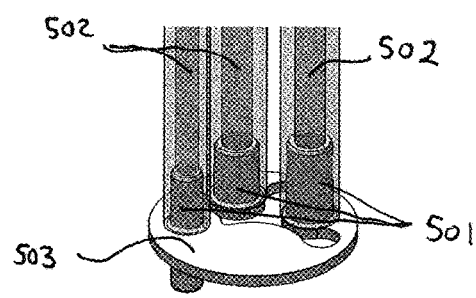
Figure 6A:
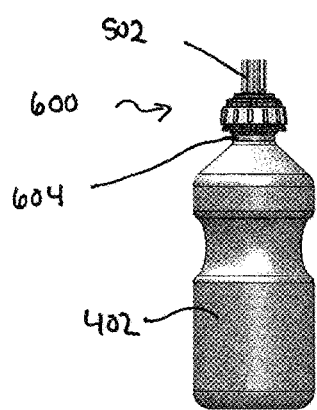
Figure 6B:
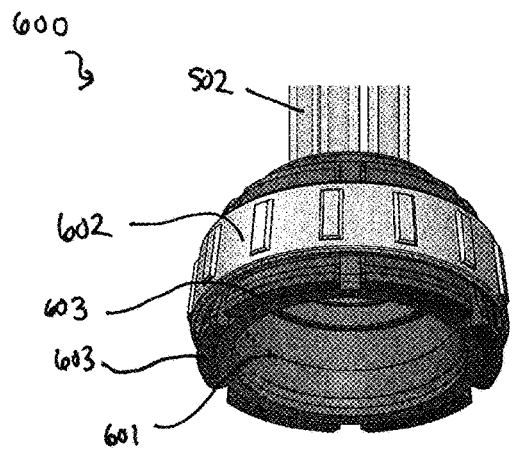
Figure 6C:
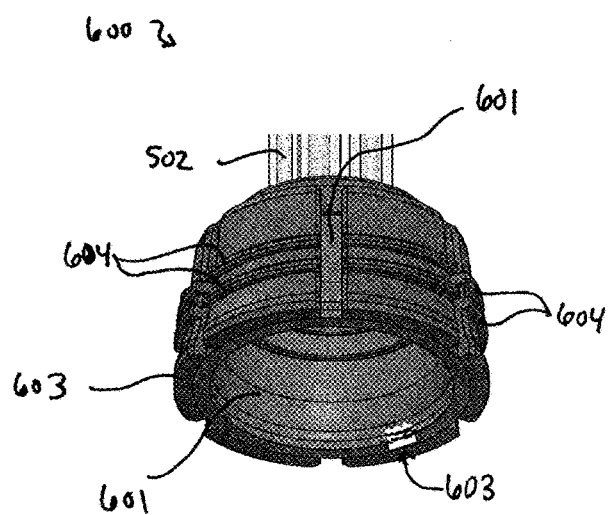
Figure 6D:
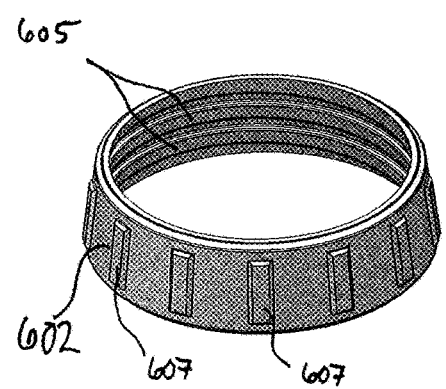
Figure 6E:
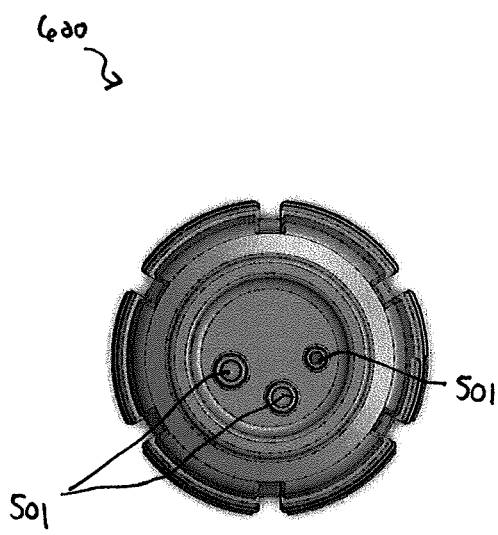
Figure 6F:
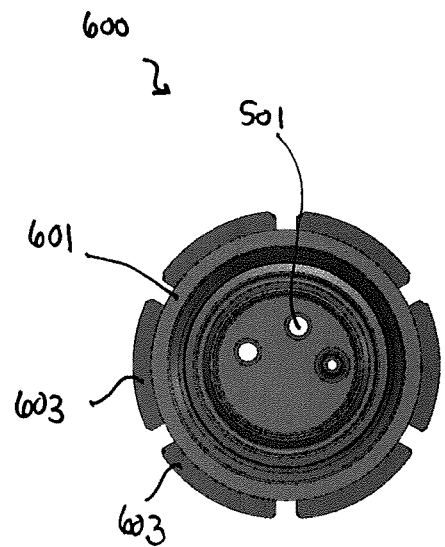
Figure 6G:
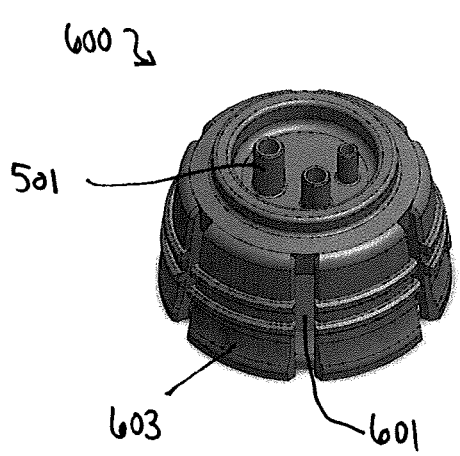
Figure 7A:
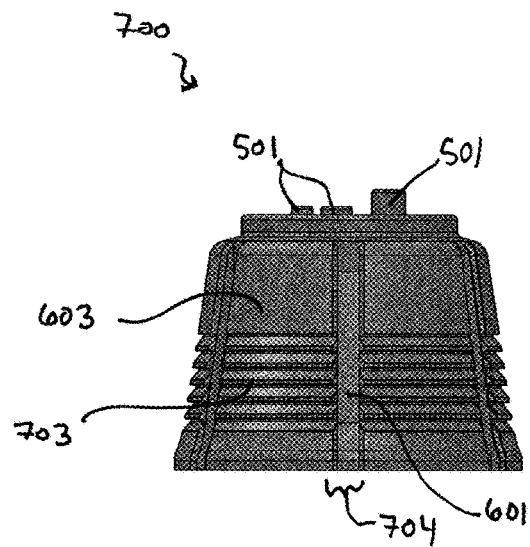
Figure 7B:
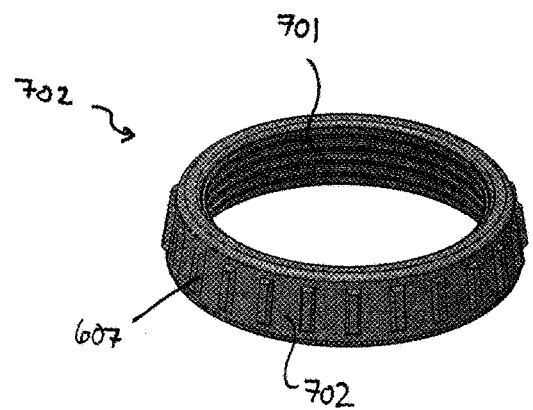
Figure 7C:
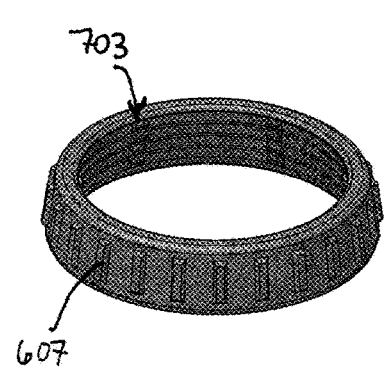
Figure 7D:
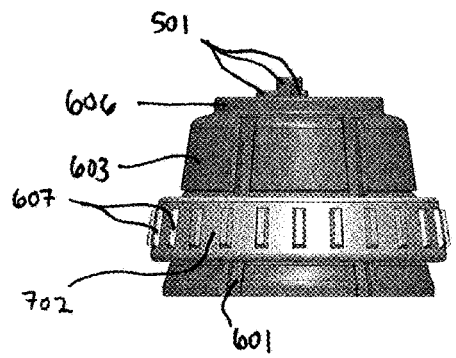
Figure 7E:
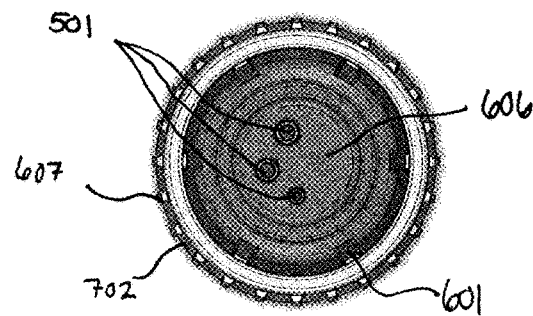
Figure 7F:
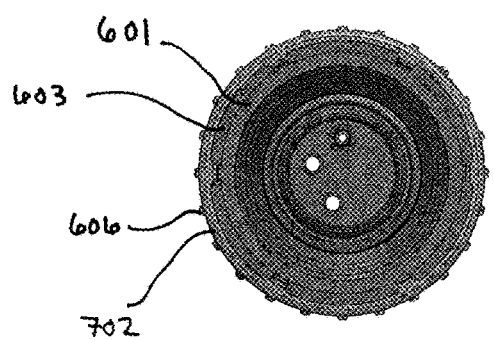
Figure 7G:
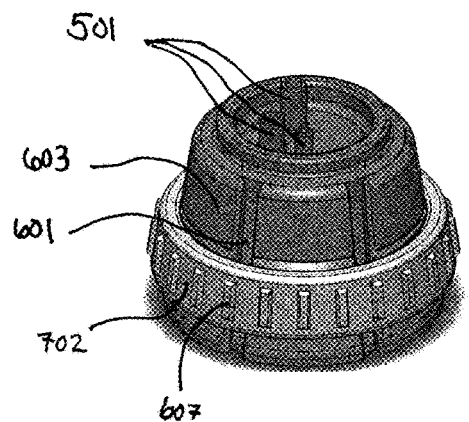
Figure 7H:
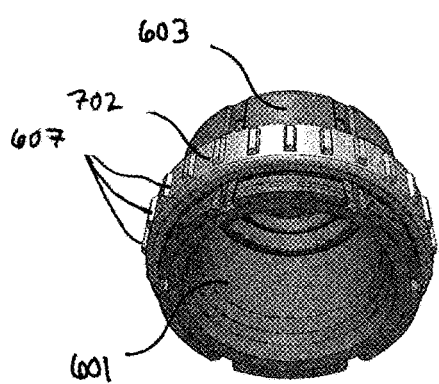
Figure 8A:
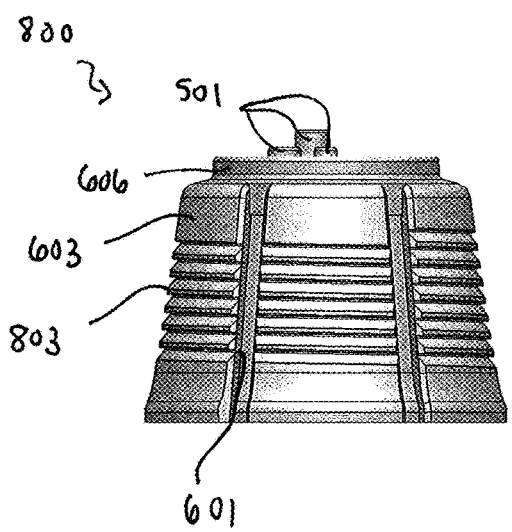
Figure 8B:
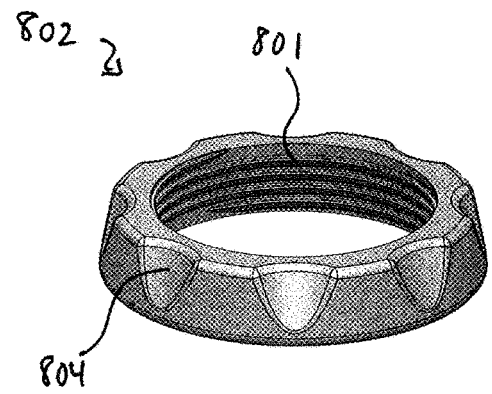
Figure 8C:
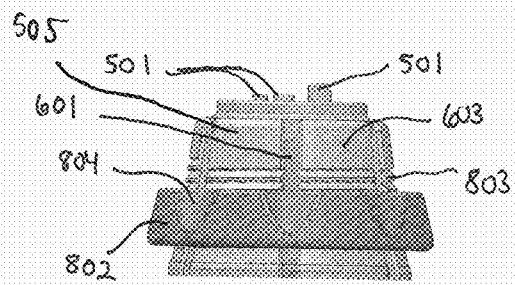
Figure 8D:
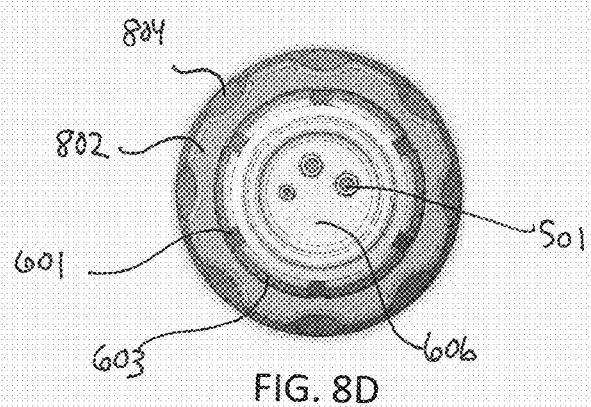
Figure 8E:
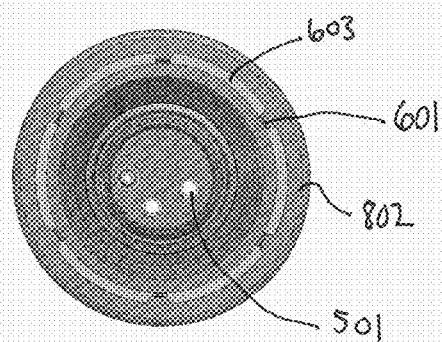
Figure 8F:
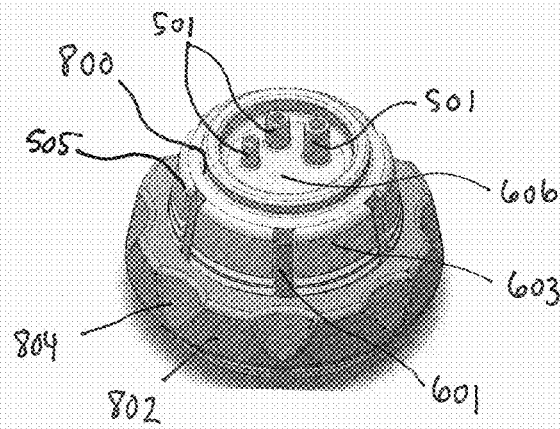
Figure 8G:
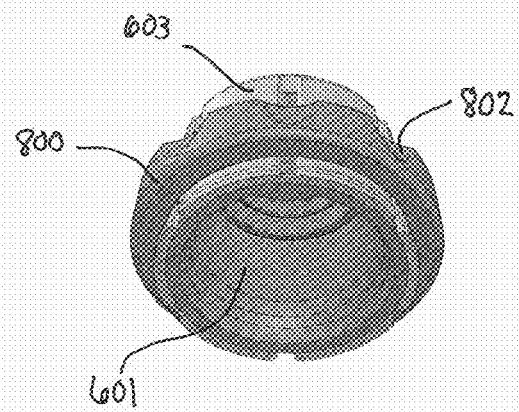
Figure 9A:
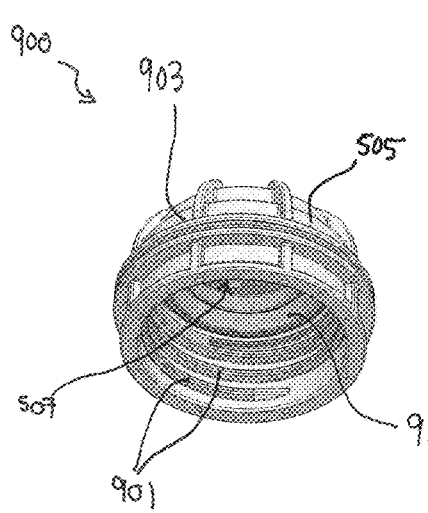
Figure 9B:
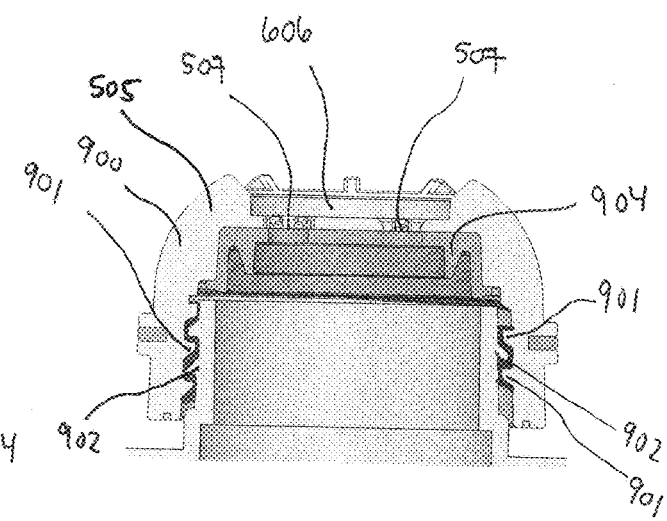
Figure 10A:
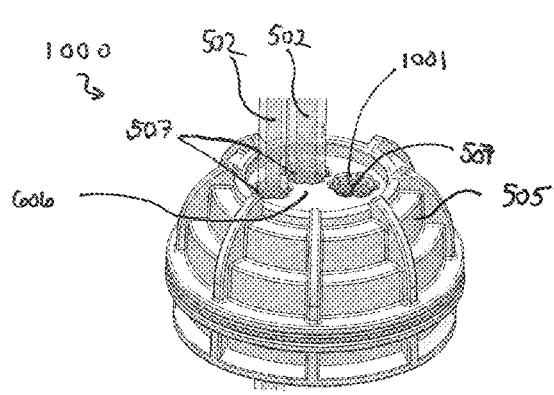
Figure 10B:
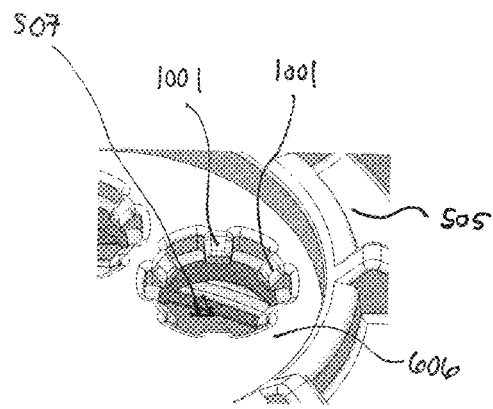
Figure 11A:
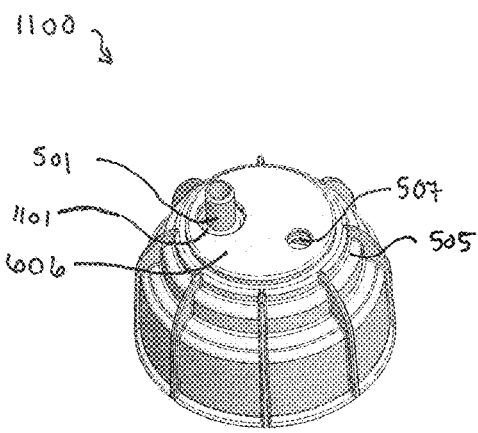
Figure 11B:
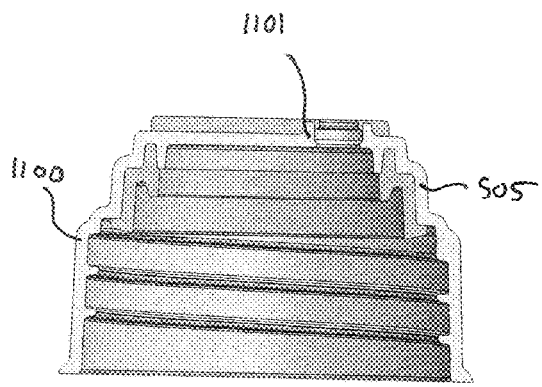
Figure 12A:
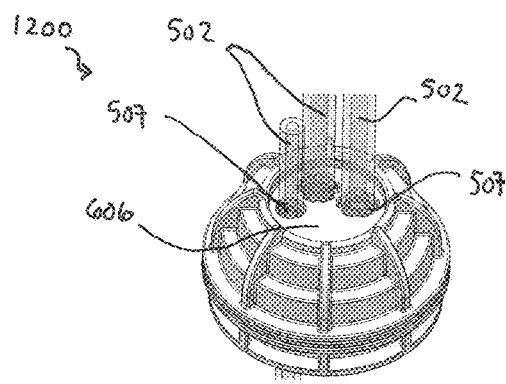
Figure 12B:
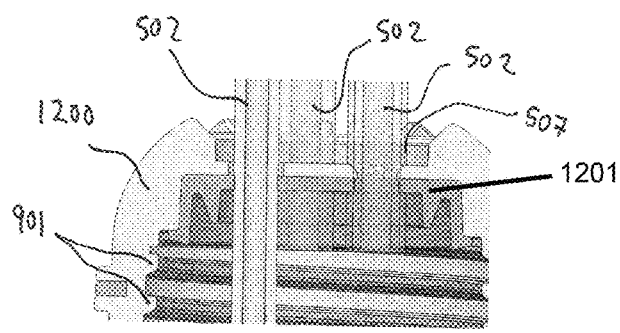
Figure 15:
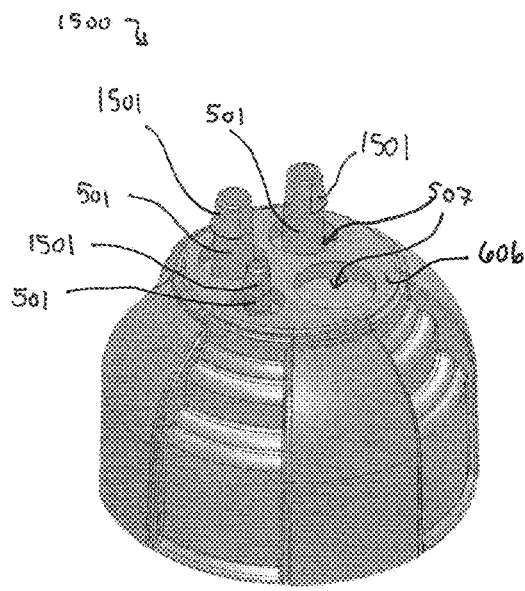
Figure 16A:
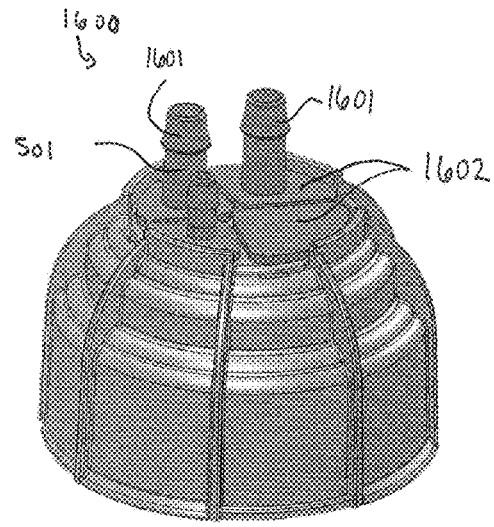
Figure 16B:
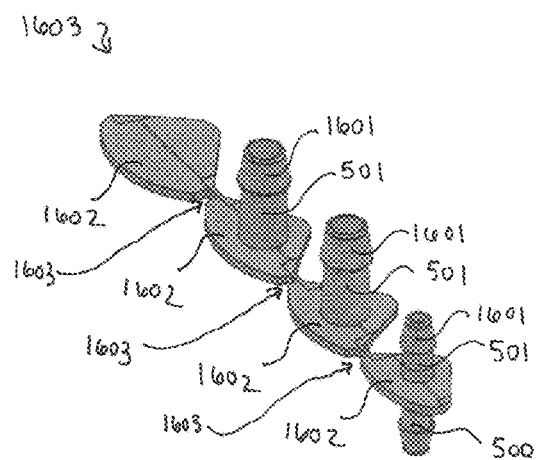
Figure 17:
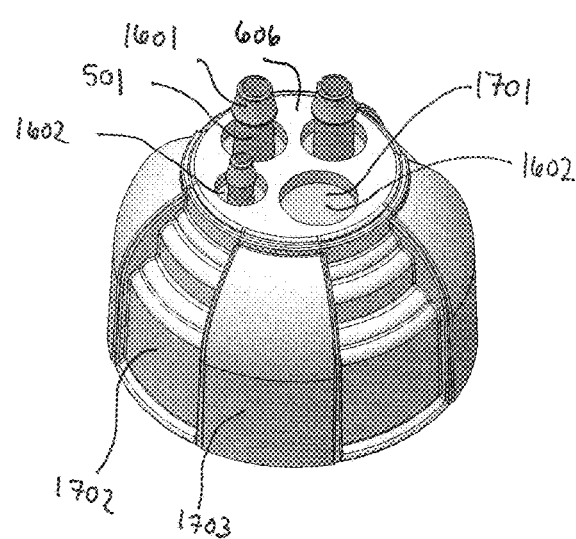
Figure 18A:
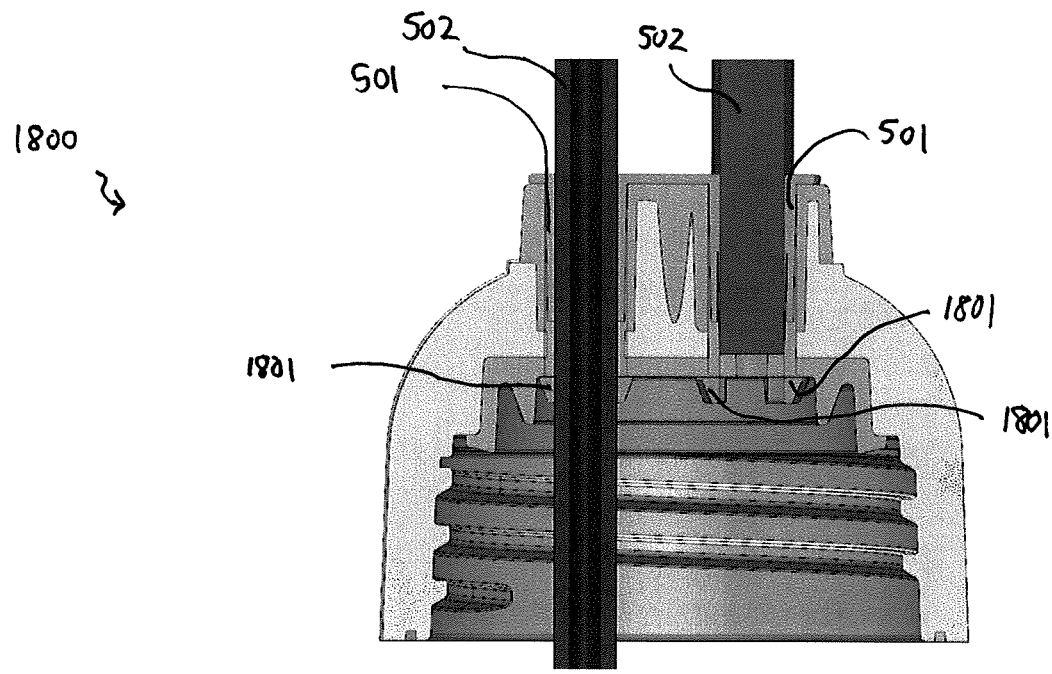
Figure 18B:
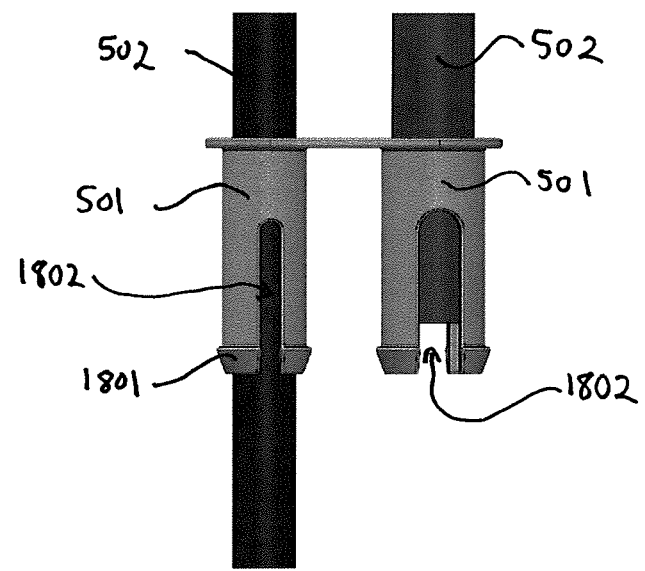
Figure 19A:
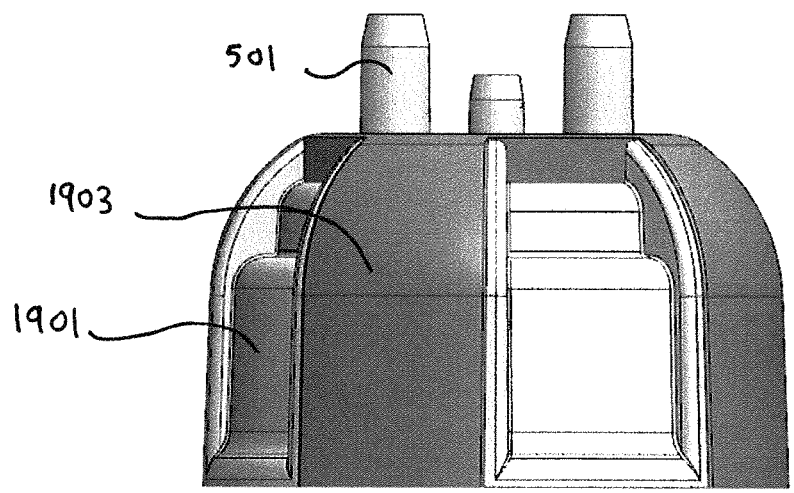
Figure 19B:
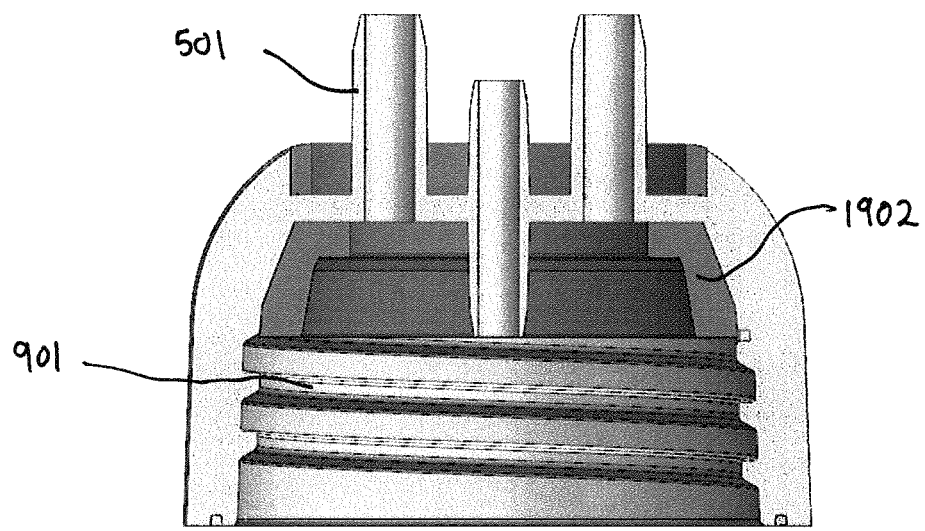
Figure 19C:
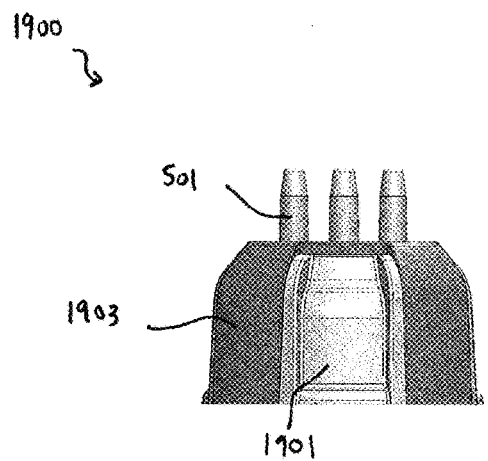
Figure 19D:
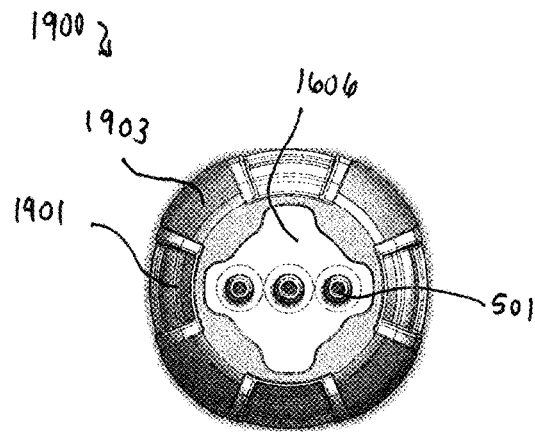
Figure 19E:
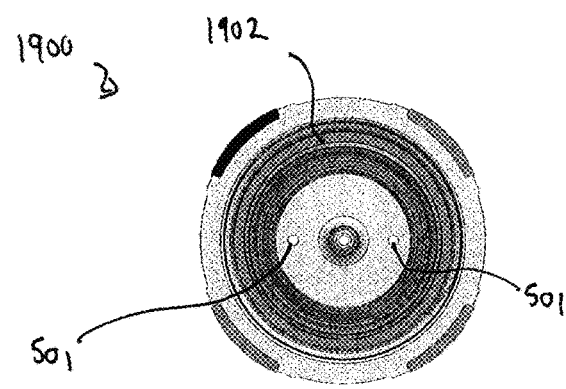
Figure 19F:
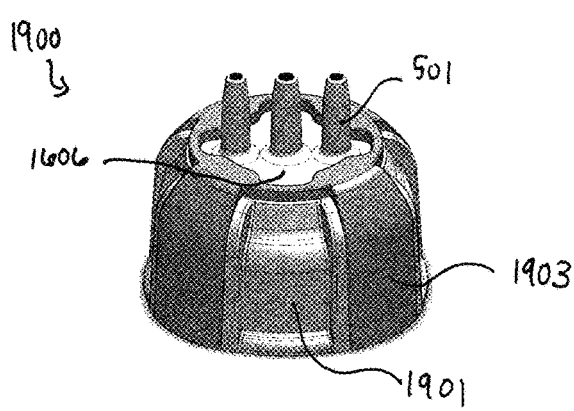
Figure 19G:
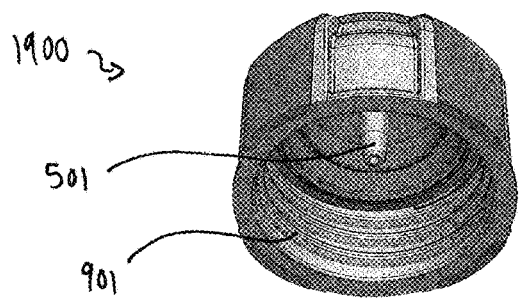
Figure 20:
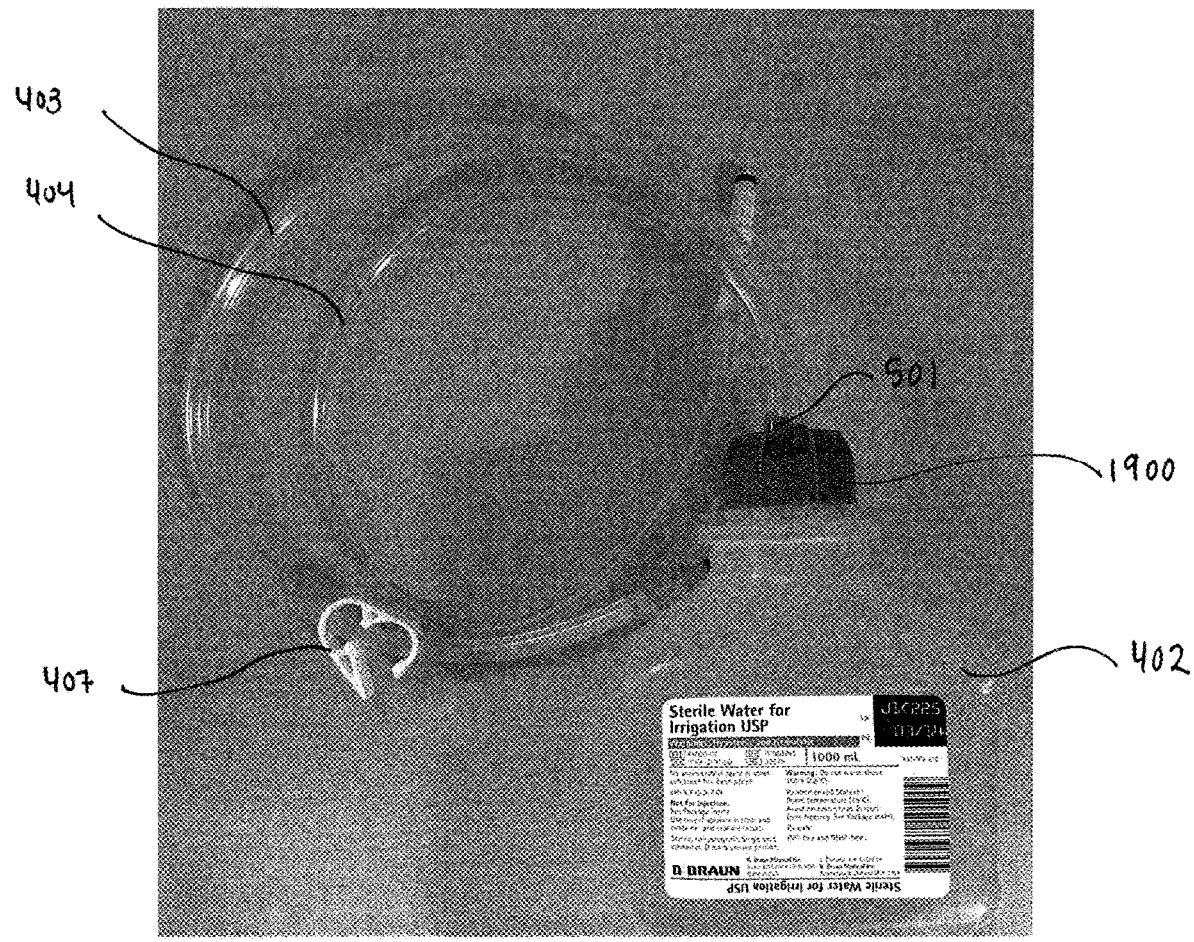
Figure 21:
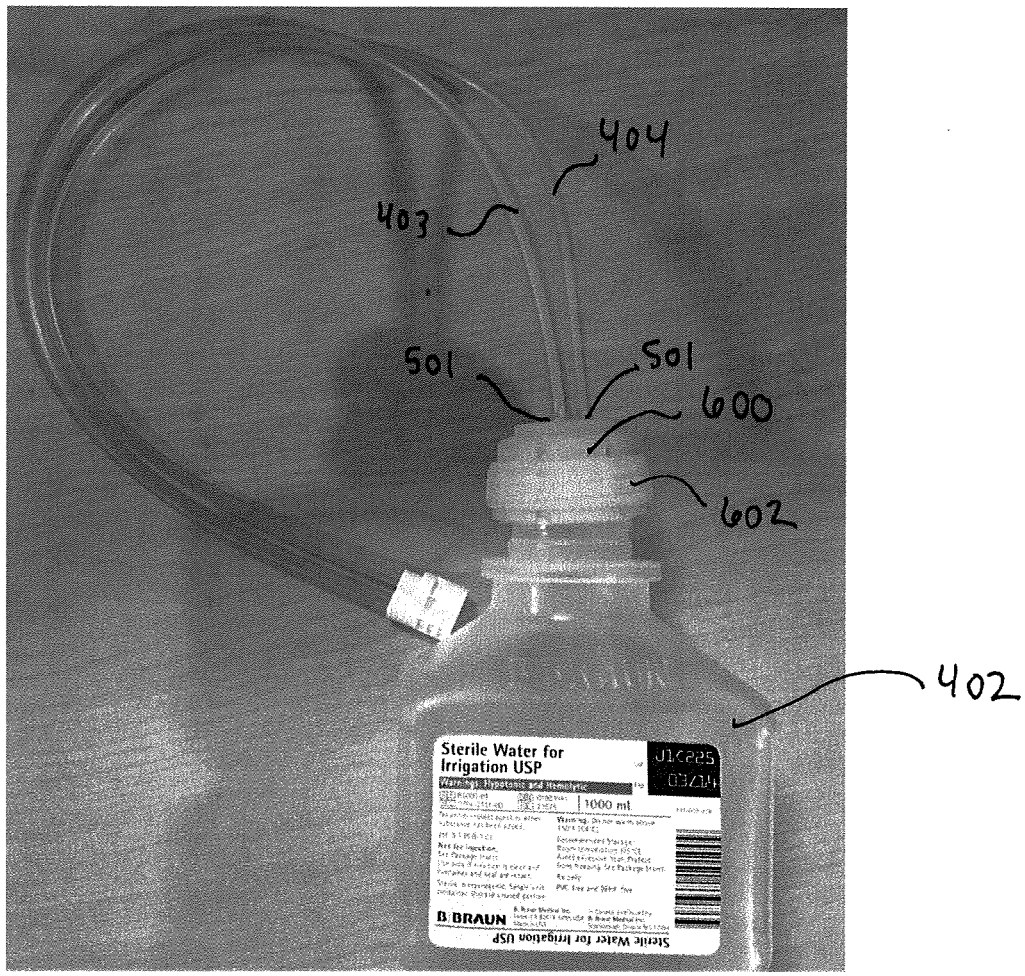
Figure 22:
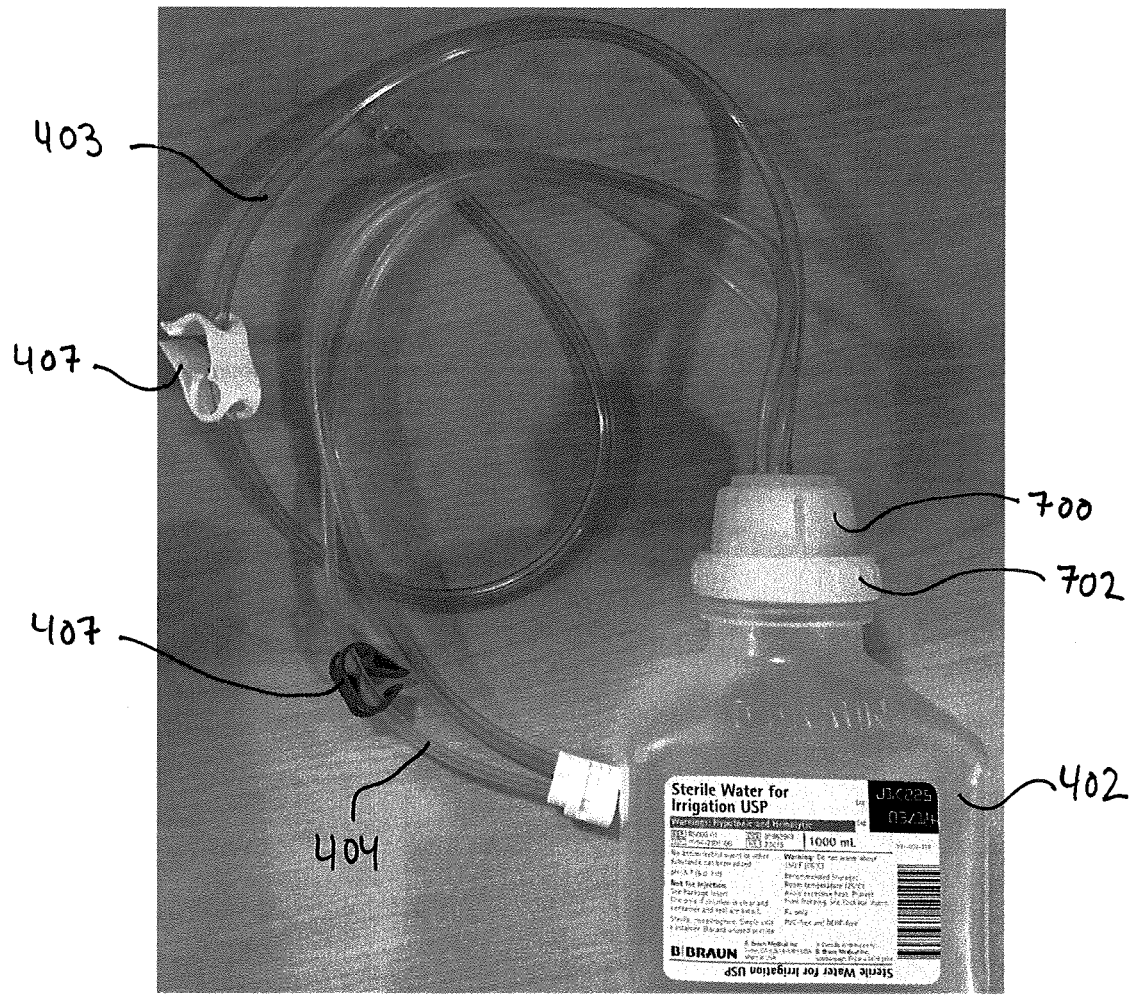
Figure 23A:
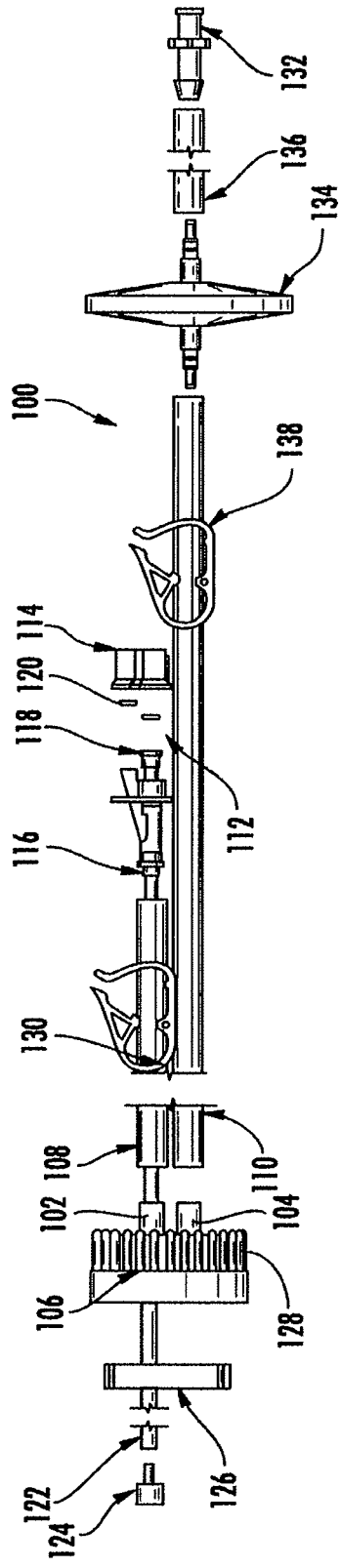
Figure 23B:
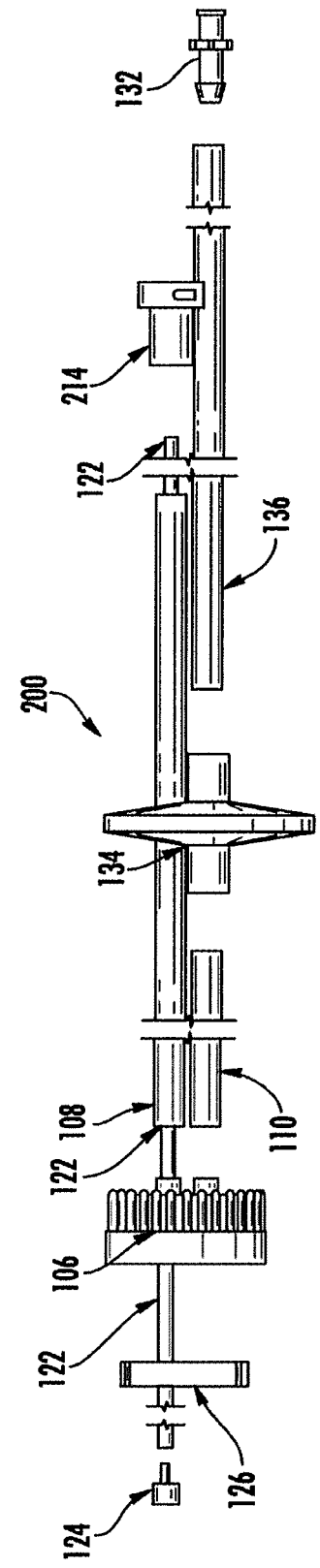
Figure 23C:
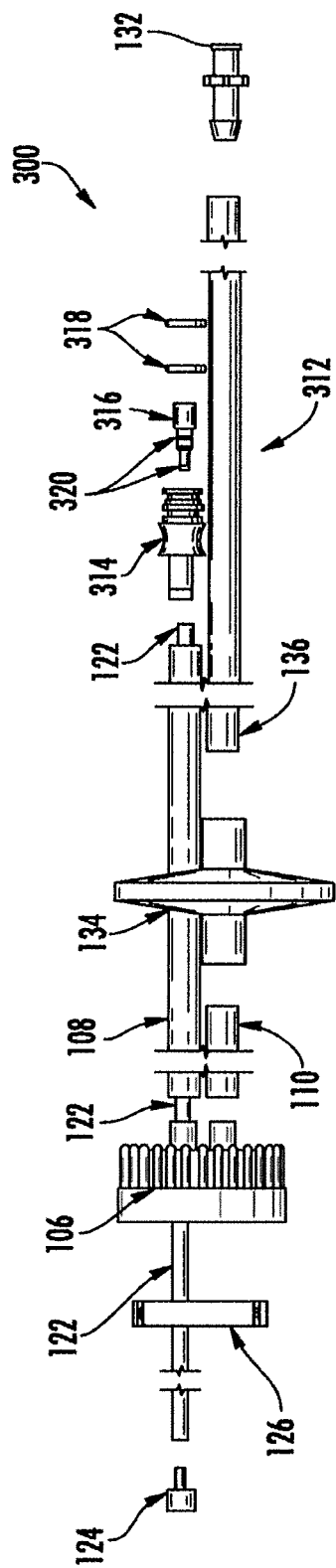
Figure 24:
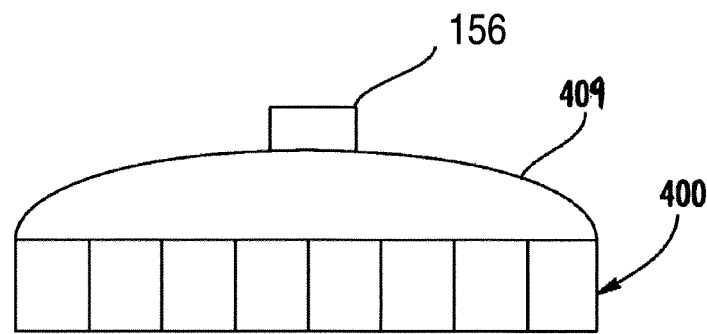
Figure 25:
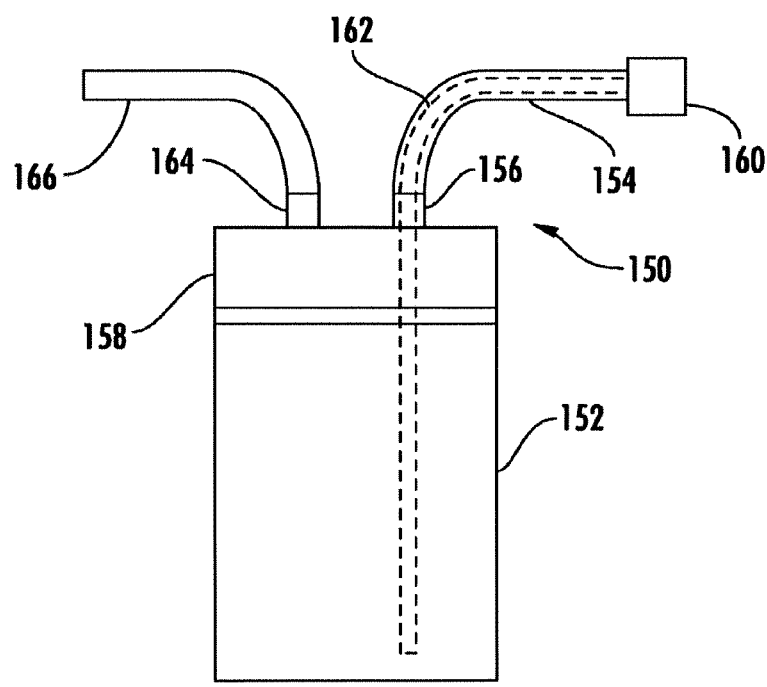

Having thus described the invention in general terms, reference will now be made to the accompanying drawings, which are not necessarily drawn to scale, and wherein:

FIG. 1 is an illustration of a conventional endoscope system;

FIG. 2 is a detailed view of the endoscope from the system illustrated in FIG. 1;

FIG. 3 is a perspective view of various adaptors configured to connect to a respective endoscopic device according to exemplary embodiments;

FIG. 4 is an illustration of a bottle cap and scope connector system;

FIG. 5A is an illustration of a bottle cap according to an exemplary embodiment;

FIG. 5B is an illustration of bosses for a bottle cap according to an exemplary embodiment;

FIG. 6A is an illustration of a bottle cap on a water bottle according to an exemplary embodiment;

FIG. 6B is an illustration of a bottle cap with collar and seal according to an exemplary embodiment;

FIG. 6C is an illustration of the cap according to the embodiment of FIG. 6B;

FIG. 6D is an illustration of a collar for a bottle cap such as the embodiment illustrated in FIG. 6B;

FIG. 6E is an illustration of the top of a cap according to the embodiment illustrated in FIG. 6B;

FIG. 6F is an illustration of the bottom of a cap, including an interior seal, according to the embodiment illustrated in FIG. 6C;

FIG. 6G is an illustration of a top down perspective view of a cap according to the embodiment of FIG. 6B;

FIG. 7A is an illustration of a bottle cap according to an exemplary embodiment;

FIG. 7B is an illustration of a collar for a bottle cap such as the embodiment illustrated in FIG. 7A;

FIG. 7C is an illustration of a collar for a bottle cap such as the embodiment illustrated in FIG. 7A;

FIG. 7D is an illustration of a side view of a cap with a collar around it such as the embodiment illustrated in FIG. 7A;

FIG. 7E is an illustration of a top view of a cap with a collar around it such as the embodiment illustrated in FIG. 7A;

FIG. 7F is a bottom view of a cap with a collar around it such as the embodiment illustrated in FIG. 7A;

FIG. 7G is a perspective view showing the top of a cap with a collar around it such as the embodiment illustrated in FIG. 7A;

FIG. 7H is a perspective view showing the bottom of a cap with a collar around it such as the embodiment illustrated in FIG. 7A;

FIG. 8A is an illustration of a bottle cap according to an exemplary embodiment;

FIG. 8B is an illustration of a collar for a bottle cap such as the embodiment illustrated in FIG. 8A;

FIG. 8C is an illustration of a bottle cap according to the embodiment illustrated in FIG. 8A with a collar around it;

FIG. 8D is a top view of the cap embodiment illustrated in FIG. 8C;

FIG. 8E is a bottom view of the cap embodiment illustrated in FIG. 8C;

FIG. 8F is a perspective view of the cap embodiment illustrated in FIG. 8C;

FIG. 8G is a perspective view of the cap embodiment illustrated in FIG. 8C;

FIG. 9A is an illustration of a bottle cap according to an exemplary embodiment;

FIG. 9B is an illustration of the bottle cap illustrated in FIG. 9A engaged with a water bottle;

FIG. 10A is an illustration of a bottle cap according to an exemplary embodiment;

FIG. 10B is a close-up view of the openings for tubing in the bottle cap illustrated in FIG. 10A;

FIG. 11A is an illustration of a bottle cap according to an exemplary embodiment;

FIG. 11B is an illustration of a cross-section of the bottle cap of FIG. 11A;

FIG. 12A is an illustration of a bottle cap according to an exemplary embodiment;

FIG. 12B is an illustration of a cross-section of a portion of the bottle cap of FIG. 12A;

FIG. 13A is an illustration of a bottle cap according to an exemplary embodiment;

FIG. 13B is an illustration of a cross-section of the bottle cap of FIG. 13A;

FIG. 14 is an illustration of a bottle cap having internal threads according to an exemplary embodiment;

FIG. 15 is an illustration of a bottle cap having partial barbs to attach to tubing according to an exemplary embodiment;

FIG. 16A is an illustration of a bottle cap having barbs to attach to tubing according to an exemplary embodiment;

FIG. 16B is an illustration of ports having barbs according to an exemplary embodiment, to be fit into a bottle cap such as that illustrated in FIG. 16A;

FIG. 17 is an illustration of molded barbs according to an exemplary embodiment, that can be attached to a bottle cap such as that in FIG. 16A;

FIG. 18A is an illustration of a cross-section of a bottle cap having tubing with overmolded barb features according to an exemplary embodiment;

FIG. 18B is an illustration of tubing with overmolded barb features according to an exemplary embodiment, to be fit into a bottle cap such as that illustrated in FIG. 18A;

FIG. 19A is an illustration of a bottle cap with press fit bosses according to an exemplary embodiment;

FIG. 19B is an illustration of a cross-section of the bottle cap of FIG. 19A;

FIG. 19C is an illustration of a bottle cap with press fit bosses according to an exemplary embodiment;

FIG. 19D is a top view of the cap embodiment illustrated in FIG. 19C;

FIG. 19E is a bottom view of the cap embodiment illustrated in FIG. 19C;

FIG. 19F is a perspective view of the cap embodiment illustrated in FIG. 19C;

FIG. 19G is a perspective view of the cap embodiment illustrated in FIG. 19C;

FIG. 20 is an illustration of a bottle cap with attached tubing, secured to a bottle, according to an exemplary embodiment;

FIG. 21 is an illustration of a bottle cap with attached tubing, secured to a bottle, according to an exemplary embodiment;

FIG. 22 is an illustration of cap with attached tubing, secured to a bottle, according to an exemplary embodiment;

FIGS. 23A-23C are exploded views of water bottle cap assemblies according to embodiments of the invention;

FIG. 24 illustrates a side view of a water bottle cap according to another embodiment of the present invention; and FIG. 25 illustrates a water bottle cap assembled with a water bottle according to one embodiment of the present invention.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", and "the", include plural referents unless the context clearly dictates otherwise.

Embodiments of the present invention are directed to water bottle cap assemblies configured for attachment between a water source and an endoscopic device during an endoscopic procedure. Endoscopic assemblies typically include a water source, such as a water bottle. In general, the water bottle cap assembly includes a cap configured to engage a water source and a tubing assembly having an adaptor configured to engage an endoscopic device. The cap may accommodate various needs for performing the endoscopic procedure using a single water source (e.g., providing water for instrument cleaning, air, a secondary gas source, and/or irrigation), while the adaptor may be varied for different types of endoscopic devices (e.g., Olympus®, Fujinon®, or Pentax® devices). Embodiments of the present invention may also be advantageous for use with a variety of disposable water bottles.

Introduction of a gas into a body cavity is common practice in gastrointestinal endoscopic procedures. Previously, when it has been desired to introduce a gas during an endoscopic procedure, standard room air was simply introduced (such as from the light source). More recently it has been found that the use of carbon dioxide ($CO_2$) insufflation can improve post-procedure patient comfort since $CO_2$ is more easily absorbed by the body. For example, use of $CO_2$ may be particularly useful for long endoscopic exams, such as endoscopic retrograde cholangiopancreatogram (ERCP), enteroscopy, and colonoscopy, and gas may be used in other endoscopic procedures as well, such as endoscopic ultrasound (EUS) and esophagogastroduodenoscopy (EGD). Provision of a secondary gas source has proven challenging, however. For example, the addition of $CO_2$ in an endoscopic procedure has previously required the use of cumbersome external regulators, flow meters, and specialized valves. The advent of specialized equipment for the provision of a secondary gas in an endoscopic procedure, such as the $CO_2$EFFICIENT® Endoscopic Insufflator (available from Bracco Diagnostics, Inc., Monroe Township, N.J.), has simplified secondary gas supply.

Different endoscopic devices are typically made by different manufacturers, thereby requiring a specific adaptor for coupling to the main body of the endoscopic device. For example, Pentax has available a gas adaptor that is designed exclusively for its endoscopic devices. Similarly Olympus and Fujinon each have specifically configured adaptors for attaching to respective endoscopic devices. According to embodiments of the present invention, each water bottle cap assembly includes an adaptor suitable for connection to a specific endoscopic device. For example, FIG. 3 illustrates a Pentax® adaptor 301, an Olympus® adaptor 302, and a Fujinon® adaptor 303. Of course, the water bottle cap assembly may be provided with other adaptor configurations depending on the endoscopic device employed. Thus, the connection of the adaptor to the endoscope main body can be facilitated in relation to the brand of endoscope. As noted previously, the three main manufacturers of endoscope devices make devices with significantly different structures. For example, a Pentax endoscope main body includes a connector with one or two pins extending from the outer surface of the connector. The Pentax® adaptor thus includes a slit for receiving the pin in rotational engagement. Alternatively, the adaptor may facilitate a press fit with the main body of the endoscopic device, such as is the case of the Pentax® and Olympus® adaptors.

Embodiments of the present invention are particularly beneficial in that the water bottle cap assemblies can be used with a wide variety of single-use, daily-use, or reusable water bottles. Generally, water bottles for use in endoscopy are of a somewhat standard size in relation to bottle volume, bottle neck diameter, and threads present. Thus, the water bottle cap assemblies of the invention can be made sized and configured to accommodate standard bottle neck sizes and threads. Thus, embodiments of the invention encompass a number of different embodiments of the water bottle cap assemblies that may vary only in the sizing of certain components of the water bottle assemblies.

Referring now to FIG. 4, an exemplary embodiment of a device including water bottle cap attached to a water bottle and attached to a water tube and an air tube, is illustrated. The water bottle cap 401 attaches to a sterile water bottle 402 to create a leak-tight seal. The device has a water tube 403 running from inside the water bottle and cap to the endoscope (not shown in FIG. 4) which allows for sterile water to be delivered to the distal end of the endoscope. The device has an air tube 404 and in some configurations, a $CO_2$ tube, which connects to the cap and the air/$CO_2$ source. These tubes (also referred to as lines) allow air and/or $CO_2$ to pressurize the bottle, which forces the water through the water tube to the distal end of the endoscope. The device has a scope connector 405 which connects the air and water tubes to the endoscope. Different configurations of the device may also consist of at least one filter 406, pinch clamp 407 to close off one or more of the water and/or air tubes, luer 408, and check valve (not shown) to provide necessary functionality as needed.

In certain exemplary embodiments, the water bottle cap can attach to the water bottle by a threadless attachment mechanism. The threadless attachment mechanism can include various seals and/or collars as described herein.

In certain exemplary embodiments, threads on the cap can be used to attach the water bottle cap to the water bottle, and a gasket and/or oversized soft threads that create interference with a water bottle can be used to create a seal around the bottle, as described herein.

In certain exemplary embodiments, the tubing can be attached to the cap without an adhesive. The tubing can be attached to the cap through the use of barbs, partial barbs, press fit bosses, and/or snap fit overmoldings, as described herein.

Referring now to FIGS. 5A and 5B, an exemplary embodiment of a water bottle cap 500 having a plurality of ports 501 on a top surface for connecting tubes (lines) 502 to the water bottle. The ports 501 can be bosses. The cap 500 in FIG. 5A has three ports 501, but in other exemplary embodiments can have two or four ports. As shown in FIG. 5B, the ports can be a part of a piece 503 that forms the top of the cap, and can be press fit or overmolded into the cap. The piece 503 can be formed with for example, polymeric materials such as polypropylene. The cap can be contoured and have overmoldings 504 on its exterior to provide a grippable surface, to facilitate rotation of the cap by a user. In FIG. 5A, contours in the cap substrate provide a grippable substrate surface 505 in addition to the overmolding. The grippable substrate surface 505 has a step-like appearance to it, in the direction from the bottom of the cap to the top, on the exterior surface of the cap. The grippable substrate surface alternates with a smooth exterior cap grippable surface in FIG. 5A, but the surfaces are not limited to this configuration. The grippable surface 504 can be overmolded on to the cap or it can be integrally formed.

In FIG. 5A, the ports protrude outwardly from the top exterior surface of the cap. The top of the cap can have a cylindrical perimeter 506 to protect the ports. The ports can be pressfit or integrally formed with the top 503 of the cap. The top 503 of the cap can then be pressfit onto the cap substrate 505. The pressfit connection between the top of the cap and the cap substrate creates a secure fit for the top and substrate components without the use of an adhesive. The ports extend a sufficient length so as to engage a tubular member for providing fluid to an endoscopic device, i.e., a tube 502 for water. The tubular member has a passageway that fluidly connects the water bottle and the endoscopic device. The fluid passageway in the tubular member is used to convey fluid between the water source and the endoscopic device. The fluid can be water or air, and can include any material that may be described in relation to flow, such as a gas or a liquid, including solutions or other physical forms of a liquid or a gas that can include some concentration of a solid material in a dissolved, suspended, or otherwise mixed state that does not prevent flow of the liquid or gas.

FIGS. 6A-6D illustrate an exemplary embodiment of a threadless water bottle cap 600, having an inner seal 601 and an outer collar 602 which locks cap flanges 603 around the water bottle top. In the exemplary embodiment shown in FIGS. 6C and 6D, the outer collar 602 can have internal threads 605 as a locking mechanism to secure the flanges of the cap on the water bottle. The inner seal 601 of the cap can be a soft inner seal, and can be made of, for example, thermoplastic elastomer or thermoset elastomer. The inner seal 601 can be overmolded onto the cap flanges 603, or alternatively, can be formed separately and attached to the cap flanges 603. The inner seal is soft and threadless, and permits a secure leak-proof attachment between a water bottle and the cap. The inner seal provides universality to the cap so that it can fit on a variety of water bottles used with endoscopes. FIG. 6A shows the cap 600 and collar 602 engaged with the top of a water bottle 402. The soft inner seal 601, visible between the flanges 603 of the cap 603, creates the seal between the cap and the water bottle. The collar 602 positioned over the cap tightens the flanges around the inner seal and water bottle top. Fluid tubes 502 can be connected to the ports of the cap. The ports can be similar to those shown in FIGS. 5A and 5B. FIG. 6B shows the cap 600 with flanges 603 having the collar 602 on it, an inner seal 601, and tubes 502 extending from the ports (not shown). FIG. 6C shows the cap 600 with flanges 603 and an inner seal 601, with tubes 502 extending from the ports (not shown). In FIG. 6C, the collar is not attached to the cap, and the cap has threading 604 on its outer surface to permit the collar to screw on to the cap. FIG. 6D shows the collar 602 which can be cylindrical or have a truncated conical shape to it. The collar can have threading 605 on its interior surface that mates with the threading 604 on the exterior of the cap. The collar can have projections 606 such as ridges or any other surface texture to provide a grip to the user when rotating the collar onto the cap.

Referring now to FIGS. 6E-6G, additional views of the cap illustrated in FIGS. 6A-6D are shown. FIG. 6E illustrates the cap from a top-down birds-eye view. The ports and top of the cap can be integrally formed with the rest of the cap. In other exemplary embodiments, the ports can be pressfit into the top of the cap. In other exemplary embodiments, the top of the cap can be pressfit on the substrate of the cap. The ports 501 on the top 606 of the cap 600 are offset from each other in the embodiment illustrated in FIGS. 6A-6G. In other exemplary embodiments, the ports can be aligned in a straight line or have other offset configurations. FIG. 6F illustrates the cap from a bottom-up view, such that the inside of the cap is shown. The inner seal 601 of the cap can cover the entire interior of the cap. The interior seal can be contoured to match the shape of the interior of the body of the cap. The inner seal can have three openings in it, that align with the ports 501. FIG. 6G illustrates a perspective view of the cap 600, without a collar on it, and the inner seal 601 can be seen from behind the flanges 603. The number of ports can vary. For example, there can be one, two, three, or four ports.

Referring now to FIGS. 7A-7C, an exemplary embodiment of a water bottle cap having flanges 603 and exemplary embodiments of collars 702, with a ratcheted locking mechanism to tighten the cap around the water bottle. FIG. 7A illustrates the cap 700 having flanges 603 extending from a top 606 of the cap. The outer circumference of the cap has a plurality of ratchets 703 that correspond to ratchets in the collar. FIG. 7B illustrates a first exemplary embodiment of a ratcheted collar 702. Ratcheted collar 702 in FIG. 7B can have a truncated cone ring shape, with full ratchets 701 surrounding the interior surface of the collar 602. In an exemplary embodiment, there can be a plurality of ratchets, including 2-10 ratchets, including 3-8 ratchets, and including 4-6 ratchets. The outer surface of the collar can have projections 606 such as ridges or any other surface texture to provide a grip to the user when rotating the collar onto the cap. In FIG. 7B, the full-circumference ratchets inside the collar permit the collar to be pressed on to the cap, and prevent it from being pulled off. With this full-circumference ratchet mechanism, the collar holds the cap onto the water bottle. The interior of the cap can be a soft inner seal 601 such as that described above with respect to FIG. 6C. The soft inner seal provides the cap with a universal fit to provide a sealed engagement with a variety of endoscope water bottles.

FIG. 7C illustrates a collar 702 similar in shape and size to the collar described above with respect to FIG. 7B, but having partial circumference ratchets 703 on the interior surface. The partial ratchets permit the collar to be pressed on to the cap 700 and twisted to align the partial circumference ratchets 703 with the spaces 704 between the flanges 603 of the cap. This alignment permits the collar to be removed. The ratchet fitting of the collar onto the cap permits the cap to have a universal fit on a variety of types of bottles. The collar can have a number of columns of partial circumference ratchets that is the same number or less than the number of flanges (and this the number of spaces between the flanges) in the cap. The collar can have a plurality of ratchet columns, including 12-2, columns, including 4-10 columns, and including 6-8 columns. In an exemplary embodiment, there can be a plurality of ratchets in each column, including 2-10 ratchets, including 3-8 ratchets, and including 4-6 ratchets. The smaller the water bottle opening is, the farther down the collar can be pressed, thus causing the flanges of the cap to move closer together to create the proper tension of fit on the water bottle to prevent leaks. The soft inner seal 601 of the cap also creates versatility and permits the cap to have a universal fit for a variety of water bottles.

Referring now to FIGS. 7D-7H, additional views of the cap 700 shown in FIG. 7A having a collar such according to one of the embodiments illustrated in FIGS. 7B and 7C, are shown. FIG. 7D illustrates a side view of the cap 700 with a collar 702 on it. The soft inner seal 601 can be seen from behind the flanges 603. FIG. 7E illustrates the cap from a top-down birds-eye view. The ports 501 on the top 606 of the cap 700 are offset from each other in this embodiment. In other exemplary embodiments, the ports can be aligned in a straight line or have other offset configurations. FIG. 7F illustrates the cap from a bottom-up view, such that the inside of the cap is shown. The inner seal 601 of the cap can cover the entire interior of the cap. The interior seal can be contoured to match the shape of the interior of the body of the cap. The inner seal can have three openings in it, that align with the ports 501. FIG. 7G illustrates a perspective view of the cap 700, with a collar on it, and the inner seal 601 can be seen from behind the flanges 603. The ports can be pressfit or integrally formed with the top 503 of the cap. The top 503 of the cap can then be pressfit onto the cap substrate 505. The pressfit connection between the top of the cap and the cap substrate creates a secure fit for the top and substrate components without the use of an adhesive. FIG. 7H illustrates another perspective view of the cap 700 with a soft inner seal 603 and a ratchet-fit collar 702 positioned over the cap. The number of ports can vary. For example, there can be one, two, three, or four ports.

Referring now to FIGS. 8A and 8B, an exemplary embodiment of a cap with a collar with a threaded ratcheted locking mechanism is illustrated. The cap 800 of FIG. 8 can have flanges 603 and threaded ratchets 803 on its outer surface, and the collar can have corresponding threaded ratchets 801 on its interior surface. The threaded ratchets 801, 803 provide a press-on, unscrew-off locking mechanism. That is, the collar 802 can be press-fit onto the cap, such that the threaded ratchets on the interior surface of the collar engage with the threaded ratchets on the exterior surface of the cap. The collar holds the flanges and a soft inner seal 601 against the water bottle opening. This cap and collar combination, with a soft inner seal inside the cap, provides a universal fit for a variety of water bottles. The threaded ratchets can be unscrewed to remove the collar from the cap, and thus remove the cap from the water bottle. The collar can have indentations 804 on it to provide a grippable surface to the user when pressing and/or screwing the collar on and/or off the cap. The collar can also have any of the projections described herein on its outer surface.

Referring now to FIGS. 8C-8G, additional views of the cap 800 and collar 802 shown in FIGS. 8A and 8B, are shown. FIG. 8C illustrates a side view of the cap 800 with a collar 802 on it. The soft inner seal 601 can be seen from behind the flanges 603. FIG. 8D illustrates the cap from a top-down birds-eye view. Portions of the inner seal 601 can be seen between the flanges 603. The ports 501 on the top 606 of the cap 800 are offset from each other in this embodiment. In other exemplary embodiments, the ports can be aligned in a straight line or have other offset configurations. The ports can be pressfit or integrally formed with the top 606 of the cap. The top 606 of the cap can then be pressfit onto the cap substrate 505. The pressfit connection between the top of the cap and the cap substrate creates a secure fit for the top and substrate components without the use of an adhesive. FIG. 8E illustrates the cap from a bottom-up view, such that the inside of the cap is shown. The inner seal 601 of the cap can cover the entire interior of the cap. The interior seal can be contoured to match the shape of the interior of the body of the cap. The inner seal can have three openings in it, that align with the ports 501. FIG. 8F illustrates a perspective view of the cap 800, with a collar on it, and the inner seal 601 can be seen from behind the flanges 603. FIG. 8G illustrates another perspective view of the cap 800 with a soft inner seal 601 and a ratchet-fit collar 802 positioned over the cap.

Referring to FIGS. 9A and 9B, a water bottle cap 900 having oversized, internal threads made of a soft material to fill in any gaps between water bottle thread and cap, to prevent any fluid leak. The cap 900 can have threads 901 on its interior surface that mate with threads 902 of a bottle opening. The cap can have a soft material cover 904 on at least some of its threads to provide a fluid tight seal with the threads on the bottle. The soft material cover 904 can be thermoplastic elastomer or thermoset elastomer. The soft material cover can be overmolded onto the threads of the cap. The soft material can make the threads appear "oversized" when connected to the threads of a bottle opening. As shown in FIG. 9A, the interior of the cap can have a soft inner seal 904 on the interior portion of the cap that is not threaded. The soft inner seal also prevents fluid from leaking between the cap and bottle. FIG. 9B illustrates a cross-section of the cap of FIG. 9A positioned on a bottle opening. The oversized soft threads form an interference fit with the threads of the bottle to create a seal. The soft inner seal 904 of the cap covers the opening of the bottle. The top of the cap 606 can have ports for a fluid tubes to connect to, as set forth in any of the exemplary embodiments described herein. The top 606 of the cap can then be pressfit onto the cap substrate 505. The pressfit connection between the top of the cap and the cap substrate creates a secure fit for the top and substrate components without the use of an adhesive.

FIGS. 10A and 10B illustrate an exemplary embodiment of a cap 1000 to be used with an endoscope system. The top 606 of the cap can have openings for tubing, such as fluid tubes 502 for air and water, to fit through. FIG. 10B illustrates a close-up view of an opening 507 with barbs 1001 on the top of the cap. The openings 507 can have barbs 1001 around the diameter of each opening, facing inward towards a center of the opening 507, to secure the tubing to the cap. The barbs can be claw-like to lock into the outer wall of tubing that is made of a soft material, for example, PVC (polyvinyl chloride) or thermoplastic elastomer. There can be one, two, three, or four openings 507. The interior of the cap can be any interior as set forth in the exemplary embodiments of bottle caps described herein. The top 606 of the cap can be pressfit onto the cap substrate 505, securing the top onto the cap without requiring use of an adhesive.

FIGS. 11A and 11B illustrate an exemplary embodiment of a cap having full circumference inner diameter barbs 1101 to secure air and water tubing. The top of the cap can have openings 507 for tubing to pass through. There can be one, two, three, or four openings. Each opening can have a barb to hold the tubing in place, in which the barb 1001 extends fully around the entire diameter of the opening, and extends inward toward a center of the opening. The barb can engage the exterior surface of a soft tube, such as that used for an air or water line extending from the bottle to an endoscope. The inner diameter barb can be used with any of the exemplary embodiments of caps described herein. Further, the top 606 of the cap can then be pressfit onto the cap substrate 505. The pressfit connection between the top of the cap and the cap substrate creates a secure fit for the top and substrate components without the use of an adhesive.

FIGS. 12A and 12B illustrate an exemplary embodiment of a cap having a plurality of openings 507 for tube connections positioned in the top 606 of the cap. FIGS. 12A and 12B illustrate three tube connections 501, but in exemplary embodiments there can be one, two, or four tube openings and tube connections. FIGS. 12A and 12B illustrate one of the openings 507 at the top 606 of the cap having an interference fit sufficient to create a snug fit to hold a fluid tube in place but that is not so tight that it immobilizes the fluid tube 502. This type of interference fit permits adjustment of the fluid tube after assembly and before or during use. The fluid tube can be the water tube that extends into the water bottle at one end, and attaches to an endoscope at its other end. In the cap illustrated in FIGS. 12A and 12B, the opening 507 has an interference fit provided by a seal 1201 made of the soft flexible inner seal material. FIGS. 12A and 12B illustrate the other ones of the openings 507 providing a snug fit with the tubes by having barbs 1001 such as those illustrated in FIG. 10B. Alternatively, the snug fit can be provided by full inner diameter barbs 1101, as illustrated in FIG. 11A. FIG. 12B, which is a cross-section of FIG. 12, illustrates the contact between the fluid tube 502 and the interference fit seal 1201. In FIG. 12B, the interior of the cap has oversized mating threads 901 covered with a soft material such as that described with respect to FIGS. 9A and 9B. However, the interference fit opening for a fluid tube can be used in any of the embodiments of cap described herein.

Referring now to FIGS. 13A and 13B, an exemplary embodiment of a cap 1300 having a gasket 1301 is illustrated. The cap can have an exterior surface according to any of the exemplary embodiments described herein. The top of the cap can be pressfit according to any of the exemplary embodiments described herein. The gasket 1301 can be made of a soft material such as thermoplastic elastomer or thermoset elastomer. The gasket can be attached to the bottom of the cap so that when the cap is attached to a bottle top, the gasket can provide a seal once the cap is fully positioned over the bottle top. FIG. 13A illustrates the position of the gasket 1301 on the bottom of the cap 1300. FIG. 13B illustrates a cross-section view of the cap in FIG. 13A, secured to a bottle opening 1302. The interior of the cap can have threads as illustrated here, or it can have any other interior structure as described herein. The gasket 1301 forms a seal between the cap 1300 and the bottle opening 1302, at the bottom of the cap and around the exterior of the bottle opening. The fluid ports 501 and the top 606 of the cap can be those according to any embodiment described herein.

Referring now to FIG. 14, an exemplary embodiment of a bottle cap 1400 having intermittent internal threads 1401 is illustrated. In this embodiment, the internal threads are intermittent, i.e., each thread does not extend across a full circumference of the interior of the cap. This can be done for an embodiment where the cap is ratcheted onto the bottle opening, and it can also be done for any embodiment where the cap is screwed on to the bottle opening with mating threads. The cap can be formed by molding. The threads can mate directly with the cap, or the threads can be oversized and coated with a soft covering, to form a seal that can fit a variety of water bottle openings.

Referring now to FIG. 15, an exemplary embodiment of a water bottle cap having a plurality of openings 507 for ports 501 to pass through, is illustrated. The ports 501 extend upward and out from the top of the cap. Fluid tubes can be attached to the ports 501. In FIG. 15, the ports each have a partial barb 1501 to attach the fluid tubes to the cap. The partial barbs each have a flange shape extending out and downward, around a portion of the top circumference of each port. The partial barbs can attach tubing to the cap without the use of an adhesive. In certain embodiments, the cap can be molded as one piece, including the ports and partial barbs. In certain embodiments, the top 606 of the cap can then be pressfit onto the cap substrate 505. The pressfit connection between the top of the cap and the cap substrate creates a secure fit for the top and substrate components without the use of an adhesive.

Referring now to FIGS. 16A and 16B, an exemplary embodiment of a cap 1600 having ports 501 with barbs 1601 is illustrated. When assembled, the ports 501 extend upward and outward from the top 606 of the cap, as shown in FIG. 16A. The barbs 1601 and ports 501 are molded as one piece, in a straight configuration as shown in FIG. 16B. The straight configuration can have bases 1602, with a port 501 on at least one base. In FIG. 16B, three of the bases 1602 have ports 501 extending in an upward direction, and each port has a barb 1601 on it. The barbs 1601 fully encircle the top of each port 501. The barbs can each be a barb that fully encircles the port, or can be a partial barb 1601 as shown in FIG. 15. In one embodiment, the same set of bases held together, at least one port can be a partial port, which is a port 501 with a partial barb 1501 and at least one port can be a fully circumferential port, which is a port 501 with a fully circumferential barb 1601. There can be one to four ports, that is, as many as one port per base. The number of ports on the bases can be the same as the desired number of ports on the cap. At least one of the ports, or more, can have a port extending below the surface of the base, into the interior of the cap when fully assembled. The exemplary embodiment shown in FIG. 16B has four bases, connected in a row by connector strands 1603. The flexible material used to make the bases and connector strands can flex so that the bases can be folded and arranged to form a circular piece that fits in the top of a cap. FIG. 16A illustrates the bases 1602 in a circular configuration placed in the top of the cap. The cap with the bases positioned on it can have an overmolded cover 1703 to secure the bases and ports in place.

FIG. 17 illustrates an exemplary embodiment of a cap with the molded bases 1602 and ports 501 of FIG. 16B and an overmolded cover 1703. The overmolded cover can have four openings 1701, even if there are only three ports in the cap. The barbs and ports can be molded from for example, polymeric materials such as polypropylene.

Referring now to FIGS. 18A and 18B, an exemplary embodiment of ports at the top of a water bottle cap is illustrated. FIG. 18A illustrates a cross-section view of a cap 1800 having two ports 501 for tubes 502 to be placed through to access an interior of a water bottle. The cap 1800 has tubular ports 501 extending downward from the top of the cap into the opening of the water bottle. As shown in FIG. 18B, the ports 501 can have barbs 1801 that snapfit into the cap to secure both the ports and the top of the cap in place. The pressfit connection between the top of the cap with ports and the cap substrate creates a secure fit without requiring the use of adhesives. Each port can have one or more cutouts 1802 along its length, to permit the port to decrease its diameter while the ports are being inserted into the cap, so that the barbs can pass through the openings and press-fit into the cap. The ports and barbs can be overmolded onto the cap. A first tube can be a water tube that passes through the port into the water bottle. A second tube can be an air tube that permits the passage of air into and/or out of the water bottle to change the internal pressure of the water bottle. Each of the tubes can be fit into the ports by being press-fit in. The ports can hold the tubes in place such that they cannot slide within the ports, and/or can be held in places so that the tubes can be adjusted once the cap is placed on a water bottle, according to any of the tube barbs or seals as described herein.

Referring now to FIGS. 19A and 19B, an exemplary embodiment of a cap having ports that are pressfit into the cap is illustrated. The cap has a substrate 1901, a seal 1902, and an overmolded exterior grip 1903. The substrate of the cap can have mating threads 901 on its interior surface that mate with the threads on the exterior surface of a water bottle opening. The seal of the cap is inside the cap, and can be positioned between the threads and the top of the cap. The top of the cap can be pressfit into the substrate of the cap according to any of the exemplary embodiments described herein, to be securely fit together without the use of an adhesive.

Referring now to FIGS. 19C-19G, additional views of the cap 1900 shown in FIGS. 19A and 19B, are shown. FIG. 19C illustrates a side view of the cap 1900, with the cap substrate 1901 and the overmolded exterior grip 1903. FIG. 19D illustrates the cap from a top-down birds-eye view. The top 1606 of the cap can be pressfit, as described above, to the cap substrate. The overmolded exterior grip 1903 can be molded over so that it at least partially covers the top of the cap. The ports 501 on the top 1606 of the cap 1900 are aligned with each other in this embodiment. In other exemplary embodiments, the ports can be aligned in an offset configuration, such as the ports in the embodiment illustrated in FIG. 8D. FIG. 19E illustrates the cap from a bottom-up view, such that the inside of the cap is shown. The overmolded exterior grip is integral with the interior flexible seal 1902 which can have a ring-like shape around the interior of the cap. FIG. 19F illustrates a perspective view of the cap 1900, with the exterior grip 1903 portions of the cap substrate 1901 and the ports 501 extending outward from the top 1606 of the cap. FIG. 19G illustrates another perspective view of the cap 1900 with interior threads 901 for attachment to a water bottle or other bottle, the interior flexible seal 1902, and one of the ports 501 extending downward into the interior of the cap.

Referring now to FIG. 20, an exemplary embodiment of a water bottle cap assembly is illustrated. In this embodiment of the assembly, there is a cap 1900, a water bottle 402, a gas supply tube 404 extending from a port 501, and a water supply tube 403 extending from another port 501. The ports can be pressfit bosses. For example, the cap 1900 in this exemplary embodiment has pressfit bosses to attach the tubing, and partial internal threads, however any exemplary embodiment of cap described herein can be used. The water supply tube 403 can be connected to a port that extends into the interior of the cap and/or water bottle. There can also be a clamp (not shown) on the gas supply tube and/or the water tube to prevent air from entering the water bottle.

Referring now to FIG. 21, another exemplary embodiment of a water bottle cap assembly is illustrated. In this embodiment of the assembly, there is a cap 600, a water bottle 402, a gas supply tube 404 extending from a port 501, and a water supply tube 403 extending from another port 501. The cap illustrated in this assembly has the features as described in the embodiment illustrated in FIGS. 6A-6G, including a collar 602 to secure the cap to the water bottle. The cap 600 in this exemplary embodiment has pressfit bosses on the ports to attach the tubing, and a soft inner seal with a threaded locking collar, however any exemplary embodiment of cap described herein can be used. The water supply tube 403 can be connected to a port that extends into the interior of the cap and/or water bottle.

Referring now to FIG. 22, another exemplary embodiment of a water bottle cap assembly is illustrated. In this embodiment of the assembly, there is a cap 700 with a collar 702 securing it to the water bottle, a water bottle 402, a gas supply tube 404 extending from a port 501, and a water supply tube 403 extending from another port 501. The cap illustrated in this assembly has the features as described in the embodiment illustrated in FIGS. 7A-7C. The cap 700 in this exemplary embodiment has pressfit bosses to attach the tubing, and a partial ratchet system to hold the collar on the flanges of the cap, however any exemplary embodiment of cap described herein can be used. The water supply tube 403 can be connected to a port that extends into the interior of the cap and/or water bottle. There can also be a clamp 407 on the gas supply tube and/or on the water supply tube to prevent air from entering the water bottle.

Furthermore, the water bottle cap assemblies shown in FIGS. 23A-23C include water bottle caps having two ports. For example, the water bottle cap assembly 100 illustrated in FIG. 23A shows two ports 102, 104 extending outwardly from the cap 106. In one embodiment, one of the ports 102 is configured to receive a dual-lumen tubular member (i.e., an outer tube 108 and an inner tube 122), while the other port 104 is configured to receive a single lumen tubular member 110. The outer tube 108 is coupled to the port 102 in a fluid-tight manner, such as using a force-fit connection. Similarly, the tubular member 110 is secured to the port 104 so as to be in fluid-tight communication. The inner tube 122 is disposed within the outer tube 108 so as to define a gap therebetween, wherein the gap is configured to convey a fluid between the water bottle and the endoscopic instrument. As such, the dual-lumen port 102 is configured to receive air between the inner tube 122 and the outer tube 108 for charging the water within the bottle for providing water through the inner tube 122 to the endoscopic instrument, while the second port 104 is configured to provide a secondary gas through the tubular member 110 to the endoscopic device. Thus, air can be provided into the water bottle to pressurize the water to convey air and/or water to the endoscopic device. The inner and/or outer tubes may be made of a variety of materials, including those that are water and $CO_2$ resistant.

FIG. 23A illustrates that the water bottle cap assembly 100 includes an adaptor assembly 112. The adaptor assembly 112 includes an adaptor 114 suitable for connection with an endoscope main body, such as that manufactured by Olympus, in a press fit. FIG. 3 shows the adaptor assembly 12 in more detail wherein a pair of openings 16, 18 are defined therethrough. The opening 16 is configured to convey water therethrough via the inner tube 122, while the opening 18 is configured to convey air therethrough via the outer tube 108. In this regard, the inner tube 122 is typically configured to receive water therethrough, while the outer tube 108 is configured to receive air therethrough. The adaptor assembly further includes a Y-adaptor 116, a peg 118, and sealing members 120 (e.g., O-rings). The peg 118 is coupled to an end of the inner tube 122 that extends through the dual-lumen port 102 and into the water bottle. The peg 118 is configured to be inserted into the Y-adaptor 116 in a force or interference fit, while the adaptor 114 is secured to the Y-adaptor so as to compress the sealing members 120 therebetween. The assembly is secured together, such as via ultrasonic welding, although other suitable securing techniques may be used.

At the opposite end of the inner tube 122 is secured a weighted tip 124, wherein the weighted tip is configured to be positioned within the water bottle. The weighted tip 124 ensures that the inner tube is positioned at or near the bottom of the water bottle in order to sufficiently utilize the volume of fluid in the water bottle. The tip 124 may also include a channel or other structure defined on its end to prevent the tip from adhering to the bottom of the water bottle due to a suction force. An additional sealing member 126, such as a gasket, in the shape of a ring may be positioned within the cap 106 for ensuring a water tight connection between the cap and the water bottle when secured together. In addition, the sealing member 126 may be formed of a resilient material (e.g., a thermoplastic elastomer) such that the sealing member is configured to facilitate connection of the cap 106 to water bottles having different sizes and threads. In particular, the sealing member 126 may be configured to absorb any slack between the threads of the cap 106 and the water bottle threads while still maintaining a hermetic seal. Moreover, an outer surface of the cap 106 may include a gripping surface 128, such as raised ribs, for facilitating rotation of the cap by a user. A clip 130 may also be provided on the outer tube 108 that is configured to close off fluid communication between the water bottle and the endoscopic device, such as at the end of a procedure.

As discussed above, the single lumen tubular member 110 is coupled to the second port 104 so as to be in fluid communication therewith. A filter 134 may disposed on the end of the tubular member 110 for preventing ingress of viruses, microbes, and other harmful foreign substances from entering the water bottle. For example, the filter may have pores of about 0.2 micron, 0.1 micron, or less. The filter 134 may also serve to prevent backflow of liquid into the gas supply unit. In some cases, the filter may be a hydrophobic filter. In some embodiments, the filter 134 may be disposed as close as possible to the water source, such as within 12 inches of the water bottle. Where a filter 134 is employed, a tubing 136 is disposed between the filter and a coupling member 132 that is configured to couple to a gas supply unit. For example, the coupling member 132 may be a luer lock or of other suitable construction (e.g., barb, press fit, threads, etc.) for allowing connection and disconnection from a gas supply device. Similar to clip 130, the tubular member 110 may also include a clip 138 that is configured to close off fluid communication between the water bottle and the gas supply device, such as at the end of a procedure.

FIG. 23B illustrates another embodiment of a water bottle cap assembly 200. The water bottle cap assembly 200 is similar to that of FIG. 23A, but includes a different adaptor 214. In this regard, the adaptor 214 is suitable for connection to the main body of a Fujinon® endoscopic device. The adaptor 214 may be integrally formed and monolithic in construction. FIG. 3 shows the adaptor 14 in further detail whereby a plurality of openings 20 in fluid communication with the outer tube 108 surround a single opening 22 in fluid communication with the inner tube 122. The adaptor 14 is configured for a twist-fit connection with the main body whereby a pair of slots 24 engage a pair of pins on the main body of the endoscopic device.

FIG. 23C illustrates another embodiment of a water bottle cap assembly 300. The water bottle cap assembly 300 is similar to that of FIGS. 23A and 23B, but includes a different adaptor assembly 312. In this regard, the adaptor assembly 312 is suitable for connection to the main body of a Pentax® endoscopic device. The adaptor assembly 312 may be configured to connect to the main body in a press-fit. In general, the adaptor assembly 312 includes an adaptor 314, an insert 316, and a pair of sealing members 318 (e.g., O-rings). The insert 316 is partially inserted within an opening of the adaptor 314 until the insert is seated on a shelf and is secured in place. The opposite end of the adaptor 314 is coupled to the inner tube 122, while the sealing members 316 are placed into wells or grooves 320 defined on the outer surface of the adaptor. FIG. 3 shows an assembled view of the adaptor assembly, wherein an opening 26 defined through the insert 316 is configured to convey water therethrough via the inner tube 122, while one or more openings 28 defined between the insert and the adaptor are configured to convey air therethrough via the outer tube 108.

FIG. 25 illustrates a simplified depiction of a water bottle cap assembly 150 engaged with a water bottle 152. As shown, an outer tube 154 is engaged with a port 156 on the cap 158. An opposite end of the outer tube 154 is engaged with an adaptor 160 for engaging a main body of an endoscopic device. An inner tube 162 extends from the adaptor 160 and into the water bottle 152. A second port 164 on the cap 158 is configured to couple to a tubular member 166, such as for providing a secondary gas source.

It is understood that the aforementioned discussion is not meant to be limiting, as the construction of the water bottle assemblies 100, 200, 300 may be modified in further embodiments. For example, the tip 124 may be eliminated where a stiffer inner tube 122 is utilized, which would improve the assembly process while also ensuring use of the entire volume of water within the water bottle. In addition, although the cap has been shown as having a planar surface, in other exemplary embodiments, the cap 400 may include a curved or domed surface 404 with at least one port 156 as shown, for example, in FIG. 24. A domed surface 409 may provide for a greater volume of air between the maximum water level height within the water bottle and the inner surface of the cap. This may prevent the currently practiced requirement of dumping out up to 33% of the volume of the water bottle to facilitate space required to reach necessary pressure levels inside of the water bottle. This feature may also allow for additional ports as more port space would be available on the cap as the surface area of the cap is increased. In addition, the water bottle cap assembly may include a check valve within the tubing (e.g., one valve per port) that could be placed within a tubular member on either side of the cap which would prevent the possibility of backflow and therefore further eliminate any chance of cross-contamination as the water bottle is used during its product lifespan. Furthermore, it is understood that the water bottle cap assemblies may include any number of adaptors for various manufacturers of endoscopic devices.

As discussed above, the water bottle cap may have one or more ports. In one embodiment, the cap may be created with all ports initially sealed off with removable sealing members and then only those ports used during a procedure would be opened. Thus, the sealing member would inhibit fluid flow through the ports. For example, the ports could be sealed off using a cap, peelable/pierceable material, or the like. This port selectability would allow for the production of a single cap configuration but allow for the assembly of multiple different products all utilizing the same cap. As such, the customer would be provided more flexibility in use of the water bottle cap, while also allowing for savings to the manufacturer in that different types of caps would be unnecessary.

The water bottle cap assemblies of the invention can be made of a variety of different materials, which may affect how the water bottle cap assemblies are formed. In general, the water bottle cap assemblies are formed of a sterilizable material (e.g., gamma sterilization). In certain embodiments, the components of the water bottle cap assemblies may be formed individually. As such, the water bottle cap assemblies particularly may comprise a plurality of individual parts that are formed separately and then combined to form the final water bottle cap assembly. Biocompatible bonding agents may also be utilized for joining components together (e.g., ultraviolet cure gamma sterilizable adhesive). Such combination can be by any means recognized as useful in the art, such as gluing, ultrasonic welding, or the like or using further attachment components, such as rivets, fasteners, or the like. It is understood that one or more components of the water bottle cap assemblies may be integrally formed. This particularly is advantageous for providing a combination of components as a single, monolithic structure, which provides for a seamless construction.

The water bottle cap assemblies of the invention are also beneficial in that they can be provided as a single-use or daily-use (e.g., disposable). For example, the water bottle assemblies may be packaged in sterile packaging and designed to be used once within a 24-hour time period after being opened. This is useful in instances where the water bottle is also disposable. In some embodiments, the inventive adaptor can be both disposable (e.g., single-use or daily-use) and reusable in that the end-user will have the option to dispose of the adaptor after a single use or at the end of the day, or to sterilize the adaptor and reuse it. This is achievable in particular because of the ability to form the water bottle cap assemblies from a variety of materials using a variety of methods. Thus, the water bottle cap assemblies can be sufficiently economical to justify making only a single use to avoid the need to sterilize. At the same time, the water bottle cap assemblies can be sufficiently sturdy to withstand multiple sterilization procedures.

The water bottle cap assemblies can be formed from a variety of different materials. In some embodiments, the water bottle cap assemblies comprise a polymeric material, which preferably is chemical resistant and/or heat resistant. The use of medical grade plastic materials is particularly desirable. Non-limiting examples of polymeric materials that may be used to form one or more component of the inventive adaptor include polyethylene (e.g., UHME-PE), polypropylene, polymethylmethacrylate (PMMA), acetal copolymers, polythermide, polycarbonate, polyvinylchloride, polysulfone (e.g., polyphenylsulfone), and polyetheretherketone (PEEK). The sealing members can be formed of any material recognized as useful in forming such elements, such as thermoplastic or natural or synthetic rubbers. It is also understood that the water bottle cap assemblies may be formed of one or more metal materials or combination of polymeric and metal materials.

Thus, embodiments of the present invention may provide several advantages. For example, the water bottle cap assemblies may be disposable and sterilizable. By providing a sterile and disposable water bottle cap assembly, cross-contamination risk is minimized and the risk associated with reprocessing errors is eliminated. Costs are thereby reduced, as reprocessing of endoscope-related accessories and components is a costly and labor intensive recurring problem that often requires a significant amount of premium floor space and capital investment. In addition, water bottle cap assemblies may support either $CO_2$ or air insufflation without the need for a water bottle dedicated to one or the other. Thus, the functionality of the interface between the tubing and the endoscopic device is derived from the cap and not from the water bottle. Therefore, the water bottle cap assemblies are configured for use with a variety of different endoscopic procedures and with different types and sizes of water bottles.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A water bottle cap comprising a substrate, a top, a collar, and a sealing member, wherein the substrate comprises:
    a plurality of flanges connected at an upper region of the substrate to form a circular upper edge of the substrate, each flange having a free end spaced apart from the free end of other flanges at a lower region of the substrate,
    an outer surface, and
    an inner surface,
    wherein the sealing member is configured to absorb slack between the inner surface and a water bottle connected to the inner surface,
    wherein the free end of each flange has a plurality of thread portions on the outer surface of the substrate,
    wherein the collar comprises a plurality of threads on an interior collar surface for mating with the plurality of thread portions of the free end of each flange,
    wherein the collar is configured to be positioned onto the outer surface of the substrate and tighten the flanges to tighten the substrate onto a water bottle opening, and
    wherein the top of the cap comprises a plurality of ports and the top is pressfit onto the substrate near the circular upper edge of the substrate.

2. The water bottle cap of claim 1, wherein the collar is configured to twist in a first direction onto the outer surface of the substrate.

3. The water bottle cap of claim 2, wherein the plurality of thread portions of the free end of each flange are angled and correspond to the threads on the interior surface of the collar.

4. The water bottle cap of claim 1, wherein the collar is configured to be pressed onto the outer surface of the substrate.

5. The water bottle cap of claim 1, wherein at least one of the ports comprises a hollow cylindrical boss and extends in a direction exterior to the top of the cap.

6. The water bottle cap of claim 1, wherein the sealing member is pliable enough to prevent fluid from passing between the inner surface and a variety of water bottle openings.

7. The water bottle cap of claim 5, wherein the hollow cylindrical boss is integrally formed with the top.

8. The water bottle cap of claim 5, wherein the hollow cylindrical boss is pressfit into the opening.

9. The water bottle cap of claim 5, wherein the hollow cylindrical boss is integrally formed with a base, such that the base is held in place and partially covered by the top.

10. The water bottle cap of claim 1, wherein the sealing member covers the entire inner surface of the substrate.

\* \* \* \* \*